(12) United States Patent
Hopkinson et al.

(10) Patent No.: US 10,688,220 B2
(45) Date of Patent: Jun. 23, 2020

(54) AMNIOTIC MEMBRANE

(71) Applicant: THE UNIVERSITY OF NOTTINGHAM, Nottingham (GB)

(72) Inventors: Andrew Hopkinson, Nottingham (GB); Matthew Branch, Nottingham (GB); Harminder Dua, Nottingham (GB); Claire Allen, Nottingham (GB)

(73) Assignee: THE UNIVERSITY OF NOTTINGHAM, Nottingham (GB)

( * ) Notice: Subject to any disclaimer, the term of this patent is extended or adjusted under 35 U.S.C. 154(b) by 596 days.

(21) Appl. No.: 14/896,147

(22) PCT Filed: Jun. 4, 2014

(86) PCT No.: PCT/GB2014/051722
§ 371 (c)(1),
(2) Date: Dec. 4, 2015

(87) PCT Pub. No.: WO2014/195699
PCT Pub. Date: Dec. 11, 2014

(65) Prior Publication Data
US 2016/0129154 A1    May 12, 2016

(30) Foreign Application Priority Data
Jun. 4, 2013 (GB) .................... 1309963.5

(51) Int. Cl.
*A61L 27/36* (2006.01)
*A61L 27/50* (2006.01)
*A61L 27/54* (2006.01)

(52) U.S. Cl.
CPC ....... *A61L 27/3691* (2013.01); *A61L 27/3604* (2013.01); *A61L 27/3641* (2013.01); *A61L 27/3687* (2013.01); *A61L 27/505* (2013.01); *A61L 27/54* (2013.01); *A61L 2430/16* (2013.01)

(58) Field of Classification Search
CPC ............. A61L 2430/16; A61L 27/3604; A61L 27/3641; A61L 27/3687; A61L 27/3691; A61L 27/505; A61L 27/54
See application file for complete search history.

(56) References Cited

FOREIGN PATENT DOCUMENTS

| EP | 1944045 A1 | 7/2008 |
|---|---|---|
| EP | 2133105 A1 | 12/2009 |

OTHER PUBLICATIONS

Rodriguez-Ares et al., "Effects of lyophilization on human amniotic membrane", Acta Ophthalmol, 87(4):396-403 (2009).
Miljudin et al. "Silica gel dissication of amniotic membrane with related epithelium cells for ocular surface reconstruction" Cell and Tissue Banking 5:271-275 (2004).
Zakaria et al., "Standardized limbal epithelial stem cell graft generation and transplantation", Tissue Engineering, 16(5):921-927 (2010).

*Primary Examiner* — Aaron J Kosar
(74) *Attorney, Agent, or Firm* — Nixon Peabody LLP; Mark J. FitzGerald

(57) ABSTRACT

The invention relates to a preserved amniotic membrane, in particular a vacuum-dried amniotic membrane. It also relates to uses of vacuum-dried amniotic membrane and methods for making a vacuum-dried amniotic membrane. A method of processing an amniotic membrane to provide a vacuum-dried amniotic membrane, comprising the step of vacuum-drying the amniotic membrane Amniotic membrane (AM) is the inner most extraembryonic membrane that surrounds the foetus in a sac of amniotic fluid, functioning as a protective barrier to ascending infection and trauma during pregnancy.

12 Claims, 19 Drawing Sheets

A

B

A

B

A

Outer packaging label prototype

Inner packaging label prototype

B

| Function | Factor | FRAM (ng/mg TP) | TTAM (ng/mg TP) | CPAM (ng/mg TP) | VDAM (ng/mg TP) | VDAM/Tre/Raff (ng/mg TP) |
|---|---|---|---|---|---|---|
| | hAng2 | 0.005 ± 0.005† | 0.000 ± 0.000* | 0.000 ± 0.0* | 0.017 ± 0.018† | 0.000 ± 0.000* |
| | hFGFbasic | 0.609 ± 0.363#* | 2.35 ± 1.559†# | 0.619 ± 0.520#* | 0.172 ± 0.068** | 1.467 ± 0.891†#* |
| Angiogenesis | hHGF | 34.004 ± 14.493†* | 84.912 ± 35.142†# | 5.313 ± 2.051** | 62.169 ± 24.638†* | 6.087 ± 2.366** |
| | hKGF | 0.106 ± 0.060† | 0.095 ± 0.082† | 0.049 ± 0.022** | 0.106 ± 0.045† | 0.179 ± 0.110†# |
| | hTIMP1 | 97.548 ± 47.431†# | 14.037 ± 7.062* | 69.815 ± 27.325*# | 59.057 ± 22.863* | 120.546 ± 60.531†# |
| | hTIMP2 | 29.566 ± 13.229* | 44.787 ± 19.990†# | 20.719 ± 9.060* | 32.132 ± 15.424* | 29.761 ± 12.655* |
| | hVEGF | 0.006 ± 0.003† | 0.007 ± 0.004† | 0.003 ± 0.003 | 0.004 ± 0.002 | 0.006 ± 0.003† |
| | hFASL | 0.003 ± 0.000* | 0.000 ± 0.000* | 0.000 ± 0.000* | 0.003 ± 0.002† | 0.000 ± 0.000* |
| | hFibrinogen | 262.972 ± 147.568†# | 24.365 ± 13.547* | 112.80 ± 48.600* | 185.786 ± 85.615*† | 224.246 ± 99.004*# |
| Biomarker | hPEDF | 85.643 ± 55.701†# | 0.000 ± 0.000* | 21.894 ± 13.005* | 28.400 ± 25.919†# | 168.303 ± 131.407*# |
| | hTRAIL | 0.104 ± 0.044†# | 0.009 ± 0.004* | 0.065 ± 0.038* | 0.090 ± 0.035† | 0.098 ± 0.044 |
| | hTSP1 | 1440.505 ± 659.289 | 23.038 ± 10.213†# | 1241.654 ± 565.711* | 1325.606 ± 762.415† | 1270.854 ± 503.243* |
| | hICAM1 | 8.830 ± 3.573* | 0.000 ± 0.000* | 7.118 ± 3.611* | 11.770 ± 5.444†* | 13.357 ± 6.568†* |
| | hICAM3 | 2.149 ± 0.911† | 4.032 ± 1.628† | 0.679 ± 0.364* | 3.911 ± 1.842† | 0.759 ± 0.293** |
| Cell Adhesion | hVCAM1 | 18.405 ± 9.258# | 0.000 ± 0.000* | 13.150 ± 5.076# | 9.709 ± 5.781* | 23.206 ± 11.844†# |
| | hE-Selectin | 0.415 ± 0.160† | 0.312 ± 0.145† | 0.176 ± 0.071** | 0.353 ± 0.148† | 0.283 ± 0.110*† |
| | hRANTES | 0.066 ± 0.031 | 0.079 ± 0.040 | 0.066 ± 0.037 | 0.164 ± 0.068† | 0.121 ± 0.060† |
| | hMIP1α | 0.078 ± 0.032† | 0.000 ± 0.000* | 0.038 ± 0.017* | 0.097 ± 0.038† | 0.077 ± 0.036† |
| Chemokine | hMIP1β | 0.023 ± 0.011 | 0.002 ± 0.001* | 0.059 ± 0.038 | 0.040 ± 0.021 | 0.063 ± 0.026 |
| | hMIF | 1762.011 ± 713.587 | 22.375 ± 16.784* | 4383.564 ± 1816.53# | 2792.842 ± 1201.670 | 3961.489 ± 1588.013* |
| | hIFNγ | 0.001 ± 0.000 | 0.000 ± 0.000 | 0.000 ± 0.0 | 0.001 ± 0.001 | 0.000 ± 0.000 |
| | hIL1α | 0.047 ± 0.021 | 0.135 ± 0.078†# | 0.073 ± 0.028* | 0.066 ± 0.030* | 0.037 ± 0.015 |
| | hIL1β | 0.001 ± 0.000 | 0.000 ± 0.000 | 0.002 ± 0.001 | 0.001 ± 0.000 | 0.000 ± 0.000 |

Figure 20

| | | | | | |
|---|---|---|---|---|---|
| Cytokine | hIL1α | 229.968 ± 100.232 | 75.830 ± 34.252* | 266.792 ± 117.48 | 301.567 ± 139.481† | 212.478 ± 85.682 |
| | hIL6 | 0.018 ± 0.008 | 0.008 ± 0.004* | 0.041 ± 0.017# | 0.028 ± 0.012 | 0.038 ± 0.003 |
| | hIL8 | 0.116 ± 0.058† | 0.144 ± 0.081† | 0.062 ± 0.036*# | 0.114 ± 0.047† | 0.146 ± 0.079† |
| | hIL10 | 0.000 ± 0.000 | 0.000 ± 0.000 | 0.000 ± 0.000 | 0.000 ± 0.000 | 0.000 ± 0.000 |
| | hTNFα | 0.006 ± 0.002† | 0.000 ± 0.000* | 0.003 ± 0.002 | 0.004 ± 0.002 | 0.002 ± 0.001 |
| | hEGF | 0.946 ± 0.429† | 0.584 ± 0.401* | 0.762 ± 0.432* | 1.123 ± 0.560† | 0.964 ± 0.396† |
| | hHBEGF | 0.000 ± 0.000 | 0.000 ± 0.000 | 0.000 ± 0.000 | 0.000 ± 0.000 | 0.000 ± 0.000 |
| | hHGH | 0.811 ± 0.444*† | 1.306 ± 1.181† | 0.098 ± 0.039*# | 1.274 ± 0.754† | 0.183 ± 0.095*† |
| | hSCF | 0.173 ± 0.069# | 0.000 ± 0.000* | 1.004 ± 0.394# | 0.138 ± 0.068 | 2.216 ± 0.885†# |
| Growth Factor | hTGFα | 0.036 ± 0.024 | 0.006 ± 0.003* | 0.049 ± 0.025 | 0.056 ± 0.047 | 0.044 ± 0.021 |
| | hTGFβ1 | 2.753 ± 1.436*# | 2.013 ± 0.817† | 1.389 ± 0.554*# | 1.714 ± 0.686*† | 6.760 ± 4.865† |
| | hTGFβ2 | 0.469 ± 0.212* | 0.808 ± 0.344 | 0.505 ± 0.249 | 0.657 ± 0.429† | 0.706 ± 0.370 |
| | hMMP1 | 0.285 ± 0.201* | 10.972 ± 6.470*# | 0.361 ± 0.242* | 0.508 ± 0.249*† | 0.574 ± 0.331† |
| | hMMP2 | 7.705 ± 3.035* | 23.204 ± 10.413†# | 8.080 ± 3.364* | 6.613 ± 3.821* | 13.905 ± 5.639†# |
| | hMMP3 | 0.194 ± 0.080† | 0.000 ± 0.000* | 0.085 ± 0.049* | 0.308 ± 0.178† | 0.383 ± 0.187† |
| Metalloprotease | hMMP7 | 0.248 ± 0.103 | 0.201 ± 0.088 | 0.390 ± 0.250 | 0.280 ± 0.126 | 0.624 ± 0.313†# |
| | hMMP8 | 0.245 ± 0.117 | 0.262 ± 0.181 | 0.727 ± 0.290# | 0.580 ± 0.346 | 0.460 ± 0.219 |
| | hMMP9 | 1.308 ± 0.523* | 2.007 ± 0.843† | 1.327 ± 0.653* | 1.749 ± 0.709† | 1.194 ± 0.511* |
| | MMP10 | 0.820 ± 0.326* | 2.032 ± 0.966*† | 1.000 ± 0.407* | 0.986 ± 0.472* | 1.216 ± 0.518† |
| | MMP13 | 0.000 ± 0.000 | 0.000 ± 0.000 | 0.000 ± 0.00 | 0.000 ± 0.0 | 0.000 ± 0.000 |
| | hBNGF | 0.003 ± 0.001 | 0.002 ± 0.001 | 0.001 ± 0.000 | 0.002 ± 0.001 | 0.003 ± 0.001 |
| | hBDNF | 1.493 ± 0.587*# | 0.372 ± 0.195*† | 0.230 ± 0.166*# | 1.174 ± 0.459† | 1.280 ± 0.547† |
| | hCNTF | 0.034 ± 0.013 | 0.000 ± 0.000* | 0.700 ± 0.486# | 0.040 ± 0.020 | 0.269 ± 0.104# |
| | hGDNF | 0.016 ± 0.019†# | 0.024 ± 0.028†# | 0.000 ± 0.0* | 0.000 ± 0.000* | 0.000 ± 0.000* |
| | hNT3 | 0.000 ± 0.000 | 0.000 ± 0.000 | 0.007 ± 0.0040# | 0.001 ± 0.000 | 0.011 ± 0.005†# |

Figure 20, cont.

AMNIOTIC MEMBRANE

CROSS-REFERENCE TO RELATED APPLICATIONS

This application is a 35 U.S.C. § 371 National Phase Entry Application of International Application No. PCT/GB2014/051722 filed Jun. 4, 2014, which designates the U.S. and claims benefit under 35 U.S.C. § 119(e) of GB Provisional Application No. 1309963.5 filed Jun. 4, 2013, the contents of each of which are incorporated herein by reference in their entireties.

This invention relates to a preserved amniotic membrane, in particular a vacuum-dried amniotic membrane. It also relates to uses of vacuum-dried amniotic membrane and methods for making a vacuum-dried amniotic membrane.

Amniotic membrane (AM) is the inner most extra embryonic membrane that surrounds the foetus in a sac of amniotic fluid, functioning as a protective barrier to ascending infection and trauma during pregnancy. AM is highly resistant to rupture and tearing, and this mechanical strength is attributed predominantly to a multilayered architecture and an extensive collagen type I network. This is separated from a single layer of cuboidal epithelium by a basement membrane (BM). The epithelium is metabolically active, maintaining amniotic fluid homeostasis and secreting embryonic stem cell factors.

AM has proven to be a highly versatile surgical adjunct. The clinical use of AM was first reported in the treatment of skin wounds, in 1910, and over the last century its application for a variety of conditions has become widespread. Today its clinical indications are diverse and AM is used as an allograft in the treatment of burns to the skin, non-healing ulcers, reconstruction of the oral cavity and bladder, a substrate for nerve regeneration and at skin graft donor sites.

Therapeutic AM is extensively used in ophthalmic surgery and was first applied with chorion, as a replacement for scarred conjunctival tissue. AM is now commonly used as a permanent graft or a temporary patch in a plethora of conjunctival and corneal procedures. These include ocular surface reconstruction and treatments for persistent epithelial defects, pterygium, bullous keratopathy and acute ocular burns. AM has been shown to act as a scaffold for cell growth, promote epithelial wound healing and to exert anti-inflammatory, anti-angiogenic, anti-fibrotic and anti-microbial effects. These mechanisms are, in part, attributed to a wide range of biological factors present in AM, for example epidermal growth factor (EGF) and transforming growth factor (TGF)-$\beta$1.

In many countries, AM is obtained from elective caesarian section deliveries and typically frozen in medium containing glycerol or dimethylsulphoxide (DMSO) while the donor is screened for a spectrum of infectious diseases. The effects of DMSO and glycerol preservatives on the structural and biochemical integrity of cryopreserved amniotic membrane (CPAM) are unclear. Following freezing AM is considered non-viable and following thawing soluble factors presumed to be beneficial are extensively depleted from the tissue, potentially reducing its efficacy. It has been additionally shown that there are significantly lower levels of angiogenic factors in CPAM compared to fresh amniotic membrane (FrAM) but they did not assess lyophilised AM. A number of studies have reported extensive depletion of soluble factors, presumed to be beneficial, from CPAM.

While frozen preparations of AM account for the majority of procedures, dried preparations have gained popularity as substrates for epithelial growth during ocular surface reconstruction, and to treat corneal perforations and leaks and pterygium. Moreover, as dried preparations can be kept at room temperature, they eliminate the need for a cold chain and are therefore suitable for use in developing countries and in military environments. Conventional freeze-drying requires the tissue to be frozen prior to drying, resulting in structural freeze damage and subsequent factor loss as observed with conventional cryopreservation techniques.

Although rehydrated dried AM has been reported to be thinner and more fragile than its cryopreserved counterpart, there is no significant difference in the tensile properties and collagenous structure of the two AM preparations.

Conventional freeze-drying requires the tissue to be frozen prior to drying. In AM, this appears to result in structural freeze damage and subsequent factor loss as compared with conventional cryopreservation techniques.

It would be advantageous to provide a dried membrane that that could be kept at room temperature and avoid the need for a cold chain but that also avoids the structural damage to the amniotic membrane and subsequent factor loss that is caused by conventional freeze drying.

It is an aim of the present invention to provide a preserved amniotic membrane that can be stored at room temperature and has minimal damage to the cellular structure so that soluble factors are retained. It is a further aim of the present invention to provide a method for processing an amniotic membrane that provides a preserved amniotic membrane that can be stored at room temperature and has minimal damage to the cellular structure so that soluble factors are retained.

Because AM is typically less than 100 microns thick, it is possible to dry it in a freeze-dryer vacuum without the pre-freeze step, and this is herein referred to as vacuum-drying.

According to a first aspect of the invention we provide a method of processing an amniotic membrane to provide a vacuum-dried amniotic membrane comprising the step of vacuum-drying the amniotic membrane.

The amniotic membrane may be collected during a natural birth or birth by caesarian section. Amniotic membranes may be vacuum-dried by spreading them flat and putting them inside a vacuum-drier.

The standard method for freeze-drying includes the step of first freezing the sample (the pre-freeze step) and then putting the frozen sample in a freeze-drier. In the standard procedure it is important to pre-freeze the sample first because the freeze-drier can only remove water that has been frozen.

Unexpectedly, because an amniotic membrane is typically less than 100 microns thick, it is possible to dry it in a freeze-dryer vacuum without the pre-freeze step. The process of drying in a freeze-dryer (also called a vacuum-drier) without a pre-freeze step is herein referred to as vacuum-drying.

The membrane is treated with one or more lyoprotectants before vacuum-drying. Any one or more lyoprotectant may be applied to the amniotic membrane before the vacuum-drying step. The amniotic membrane may be soaked or dipped in a solution of the lyoprotectant. The lyoprotectant may be any suitable lyoprotectant, for example a saccharide lyoprotectant, for example the lyoprotectant may be trehalose dihydrate and/or raffinose pentahydrate. The lyoprotectant may be trehalose or raffinose in combination with one or more further lyoprotectants. More than one lyoprotectant may be applied to the amniotic membrane before vacuum-drying. A combination of two or more, three or more, four or more or five or more or six or more lyoprotectants may be applied to the amniotic membrane before vacuum-drying.

The amniotic membrane may be treated with an antioxidant before vacuum-drying. For example, the antioxidant is epigallocatechin (EGCG).

In addition to lyoprotectans and antioxidants the amniotic membrane may be treated with other agents before vacuum-drying. For example the amniotic membrane may be treated with glycerol/PBS, DMSO, PBS, tertiary butyl alcohol, or trehalose.

Prior to vacuum-drying the membrane may be washed to remove blood or debris, spread out flat and/or cut into sections. Membrane sections may be washed in a 1:10 dilution of the original saccharide lyoprotectant to remove excess residue from the surface.

The amniotic membrane may be not frozen before the vacuum-drying step. The amniotic membrane should not be frozen before the vacuum-drying step in the method of the present invention. Freezing the amniotic membrane before vacuum-drying (pre-freeze step) damages the structure and/or may damage the cells in the amniotic membrane. Damage to the cells in the amniotic membrane may cause increased soluble factors to be lost when the membrane is reconstituted. Damage to the cells in the amniotic membrane may lead to soluble factors being released quickly from the amniotic membrane when it is reconstituted. It is advantageous to vacuum-dry the amniotic membrane without a pre-freeze step because this causes less damage to the amniotic membrane than when a pre-freeze step is used. The vacuum-dried amniotic membrane has similar structure to fresh amniotic membrane.

The epithelial cells of the amniotic membrane may make soluble factors including growth factors. The epithelial cells may be damaged by freezing and thawing and the damaged cells may release all of the soluble factors at once. In vacuum-dried amniotic membrane the epithelial cells are not damaged by freezing and they retain soluble factors involved in cell growth and motility, for example hepatocyte growth factor (HGF); anti-angiogenesis, pigment epithelium-derived factor (PEDF); cell adhesion, intercellular adhesion molecule-1 (ICAM-1); inflammation, interleukin-8 (IL-8); cell growth and differentiation, epidermal growth factor (EGF); structural remodelling, metalloproteases 3 and 9 (MMP-3/9); and neuron growth and differentiation, brain-derived neurotrophic factor (BDNF), which are released more slowly and over a longer period of time from epithelial cells that are not damaged. Vacuum-dried and reconstituted amniotic membrane comprising epithelial cells releases soluble factors over a period of at least a day, at least two days, at least three days, at least four days, at least five days, at least 6 days, at least 7 days, at least 8 days, at least 9 days or at least 10 days. This is in contrast to prior part frozen amniotic membranes, which release most of their soluble factors in the first 24 hours.

It is advantageous to release growth factors over a period of several days, for example two or more days, because they can support healing of tissues that are in contact with the amniotic membrane for several days.

The amniotic membrane may be treated with thermolysin before vacuum-drying. Thermolysin removes the epithelial cells from the amniotic membrane to provide a denuded amniotic membrane.

If the amniotic membrane is to be used for tissue engineering, cells may be grown on the amniotic ex vivo. It may be helpful to use a denuded amniotic membrane, for example, for tissue engineering purposes where cells are grown on the amniotic membrane ex vivo or in vivo. The membrane may be denuded by treating the fresh membrane with thermolysin before vacuum-drying.

A method for providing a vacuum-dried denuded amniotic membrane may therefore comprise the steps of treating the amniotic membrane with thermolysin and vacuum-drying the amniotic membrane. The step of treating the amniotic membrane with thermolysin may be performed before the step of freeze-drying the amniotic membrane.

The amniotic membrane may be treated with thermolysin by incubating processed sections of amniotic membrane with thermolysin at a suitable concentration, for example 125 µg/ml, for a suitable amount of time to remove the epithelial cells, for example 9 minutes, with gentle agitation. Amnion sections may then be washed in Dulbecco's phosphate buffered saline (DPBS) prior to drying.

The method may include further steps before or after the membrane has been vacuum dried. Further steps may include cutting the amniotic membrane to a suitable size and shape either before or after vacuum-drying; vacuum-packing the vacuum-dried amniotic membrane after drying and sterilising the amniotic membrane either before or after vacuum-drying.

In a second aspect the present invention provides vacuum-dried amniotic membrane prepared using a method according to the present invention.

The advantage of a vacuum-dried membrane prepared according to the present invention is that the membrane structure is not damaged by freezing. The membrane may retain more soluble factors compared to a membrane that has been frozen. A vacuum-dried amniotic membrane may comprise 100% of the soluble factors compared to a fresh amniotic membrane. A vacuum-dried amniotic membrane may comprise more than 90%, more than 80%, more than 70%, more than 60%, more than 50%, more than 40%, or more than 30% of the soluble factors compared to a fresh amniotic membrane.

A vacuum-dried membrane may release soluble factors over a period of more than a day, more than 2 days, more than 3 days, more than 4 days, more than 5 days, more than 6 days, more than 7 days, more than 8 days, more than 10 days, more than 12 days, more than 14 days. A vacuum-dried membrane may release soluble factors over a period of 5 to 7 days.

This is advantageous over a cryo preserved membrane, which may release all of its soluble factors in 24 hours.

In a further aspect the present invention provides a denuded vacuum-dried amniotic membrane prepared by the method according to the present invention.

In a further aspect a vacuum-dried amniotic membrane prepared according to the present invention may be used in a variety of applications. For example, a vacuum-dried amniotic membrane may be used in human or veterinary medicine, in particular a vacuum-dried amniotic membrane may be used in treatment of diseases or damage to the eye or in wound-healing following trauma or surgery or for tissue engineering. A vacuum-dried amniotic membrane may be reconstituted by adding a suitable amount of water or a suitable biocompatible solution to the membrane for a suitable time until the membrane has become rehydrated. A vacuum-dried amniotic membrane may be reconstituted by placing it directly on the eye or on a wound or operation site with or without adding liquid directly to the amniotic membrane first. Liquid naturally occurring in the eye, wound or operation site for example tears, tissue fluid, blood or liquid added to the eye, wound or operation site may reconstitute the vacuum-dried amniotic membrane while it is in contact with the surface of the eye, wound or operation site. This is particularly advantageous in emergency situations and situations where the vacuum-dried amniotic membrane needs to be applied outside of a medical environment, for example in a combat zone, expedition or sporting event. Applying the vacuum-dried amniotic membrane directly to the eye without reconstituting is advantageous to save time and to avoid contamination of the vacuum-dried amniotic membrane while it is being reconstituted.

After the vacuum-dried amniotic membrane has been applied to the eye it may be kept in place by sutures, fibrin gluing or by a conformer shell that is applied to the eye surface over the vacuum-dried amniotic membrane. The shell may be made of any suitable material, for example plastic and may be shaped to fit over the surface of the eye. Applying a shell over the amniotic membrane may keep the amniotic membrane in place on the surface of the eye and may avoid the need to suture the amniotic membrane to the eye.

A vacuum-dried amniotic membrane prepared using the method of the present invention may be used for treatment of wounds.

There now follows by way of example only a detailed description of the present invention with reference to the accompanying drawings, in which.

Figure 3:
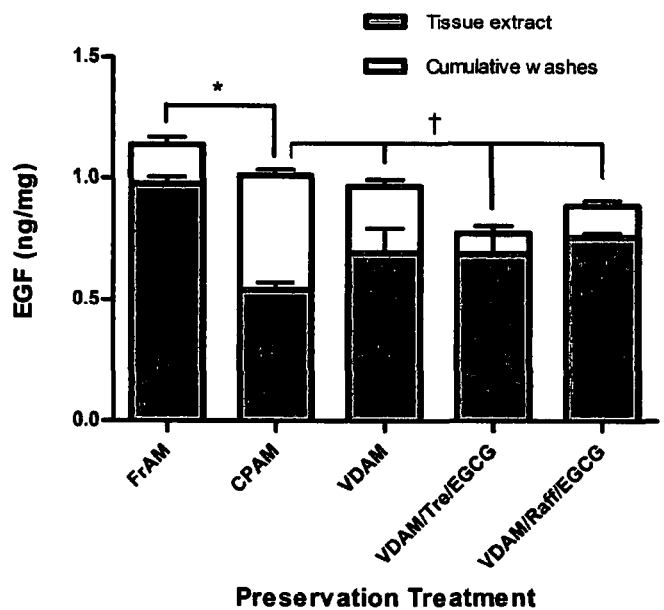
Figure 3:
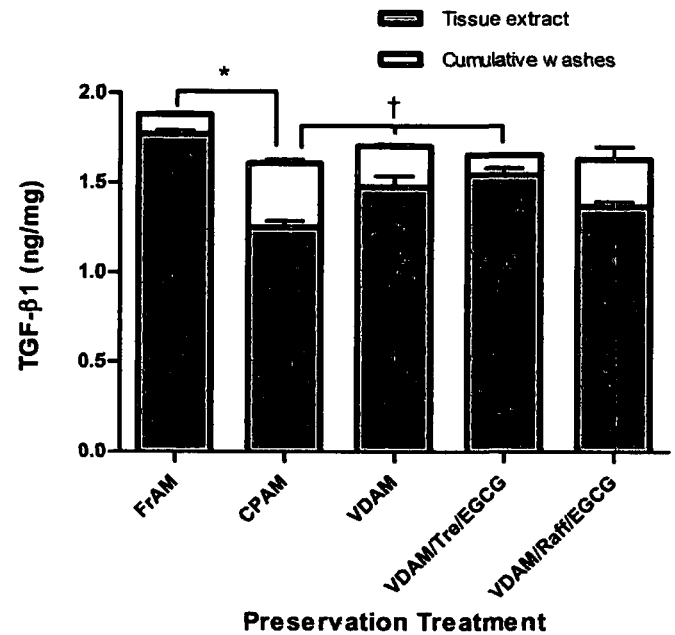
Figure 4:
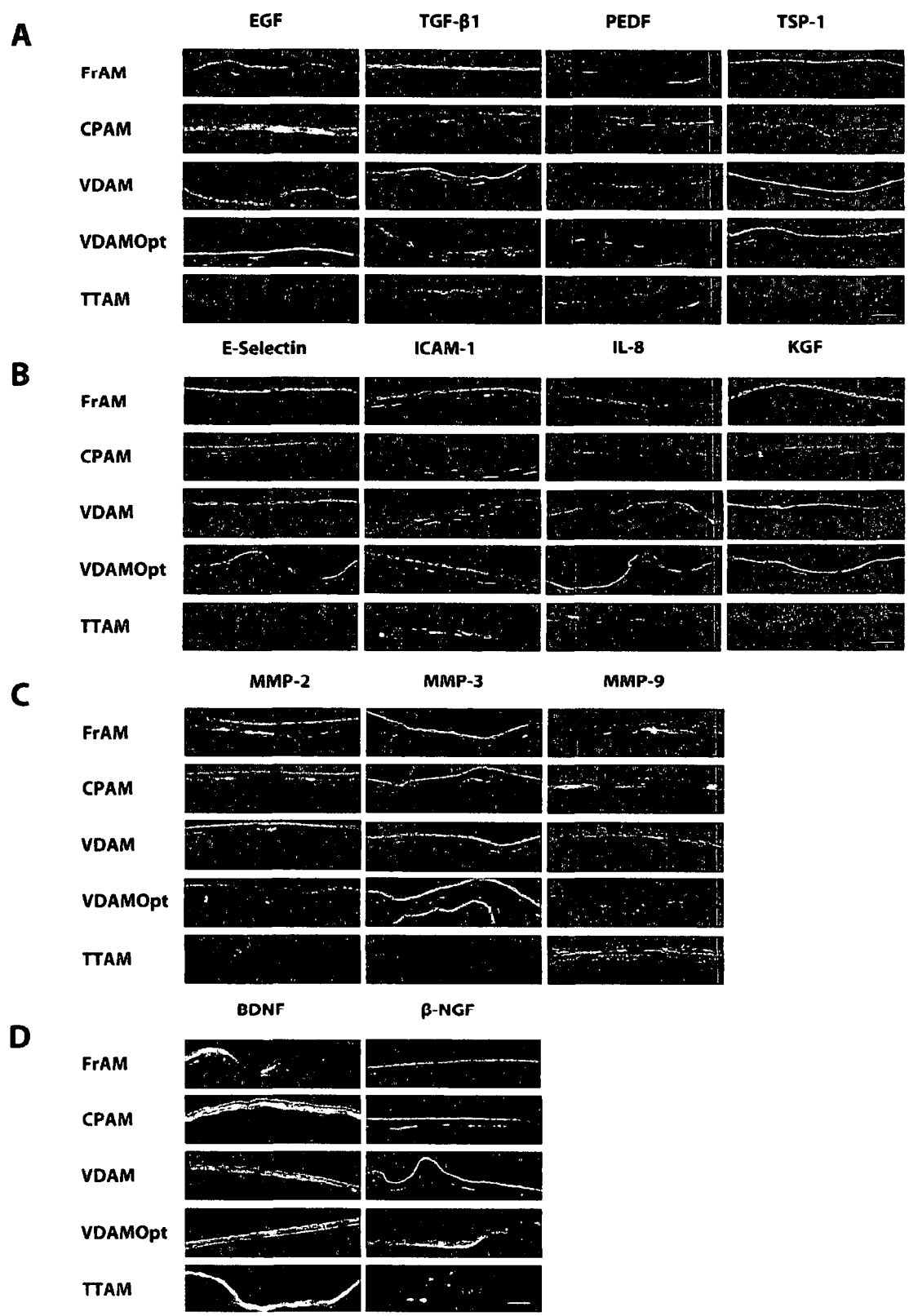
Figure 5:
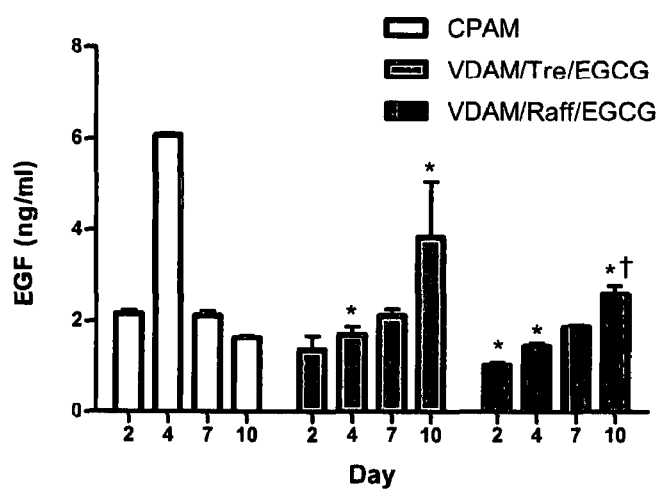
Figure 5:
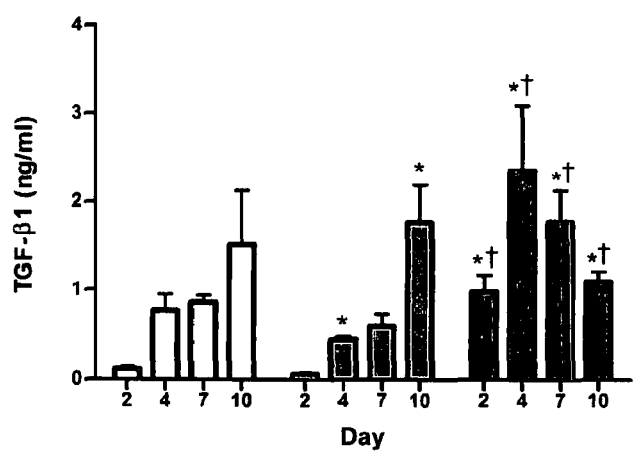
Figure 6:
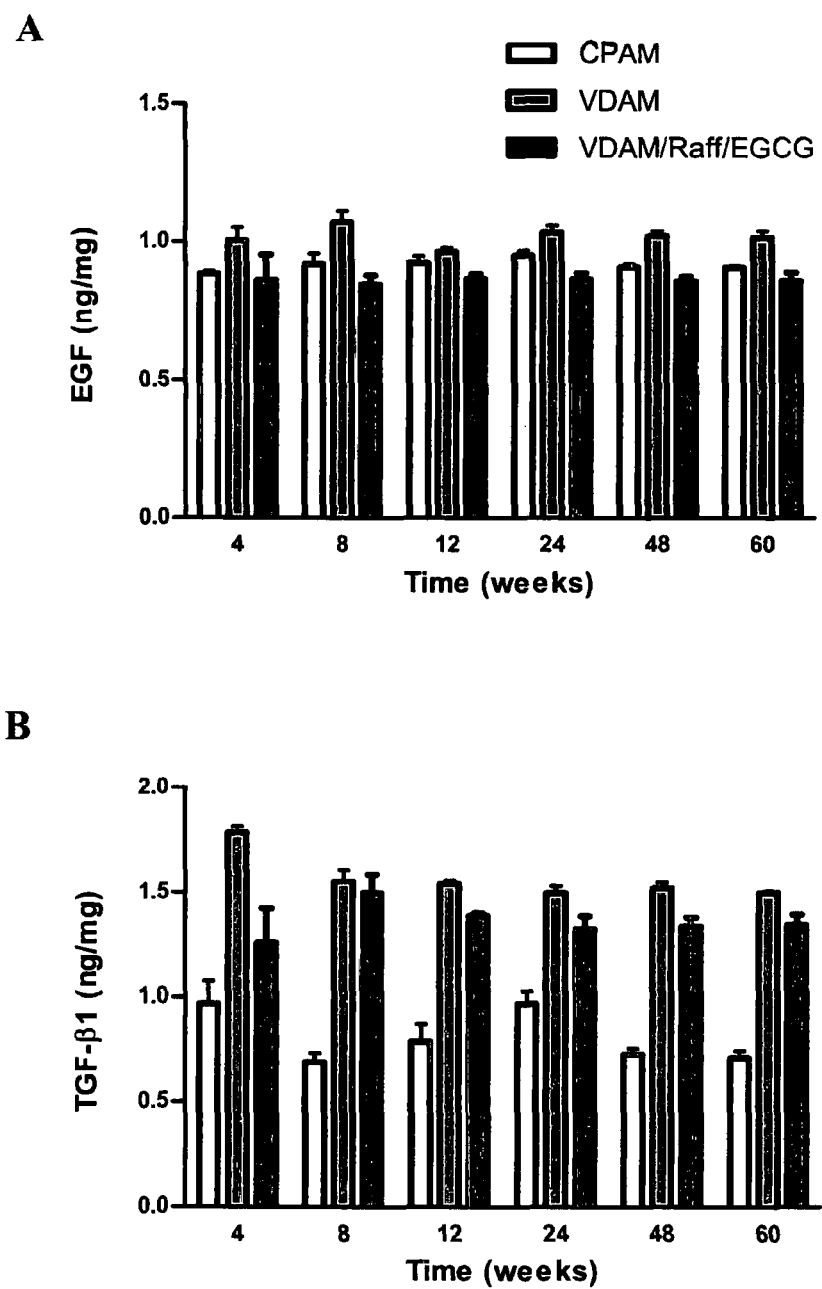
Figure 7:
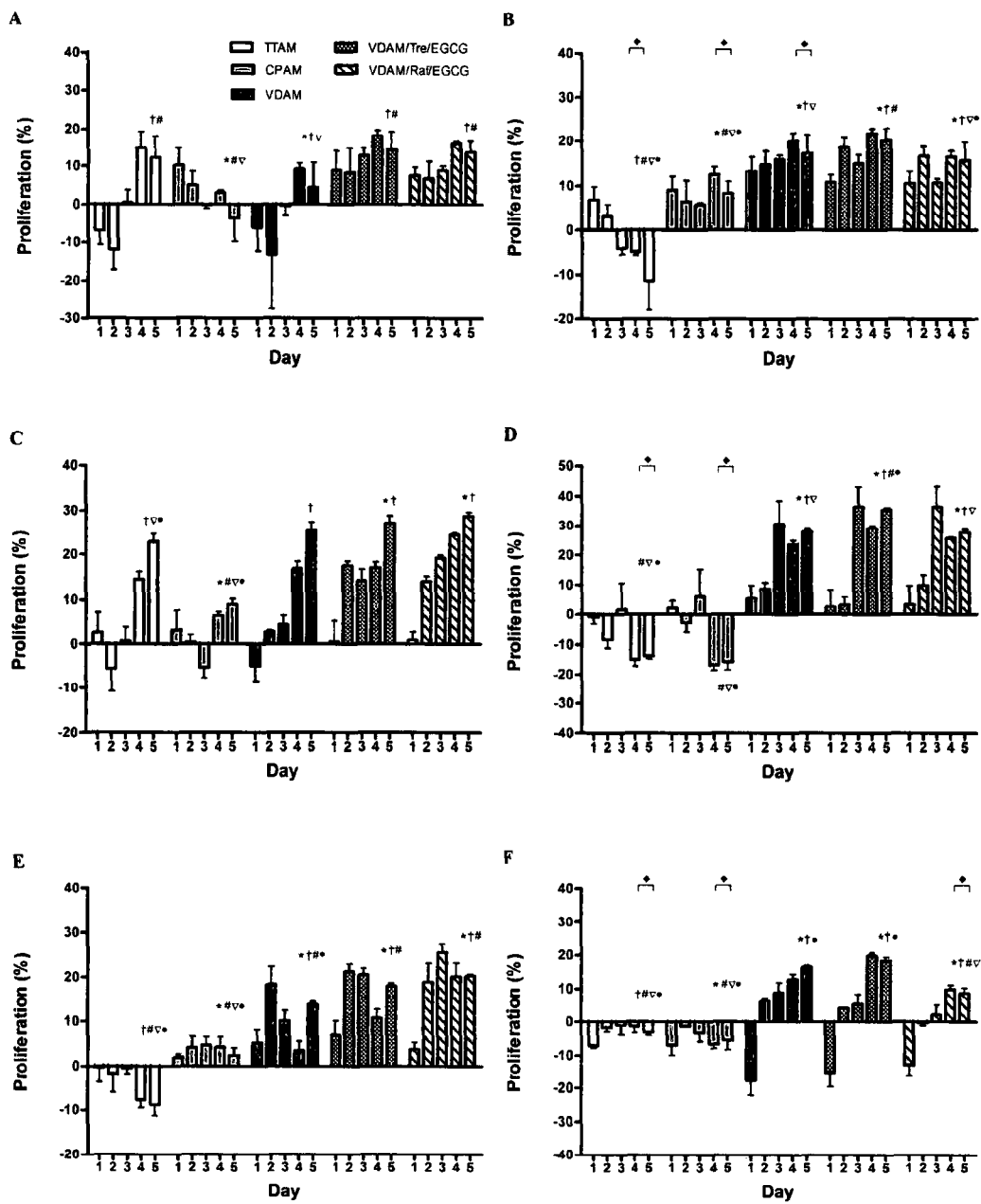
Figure 8:
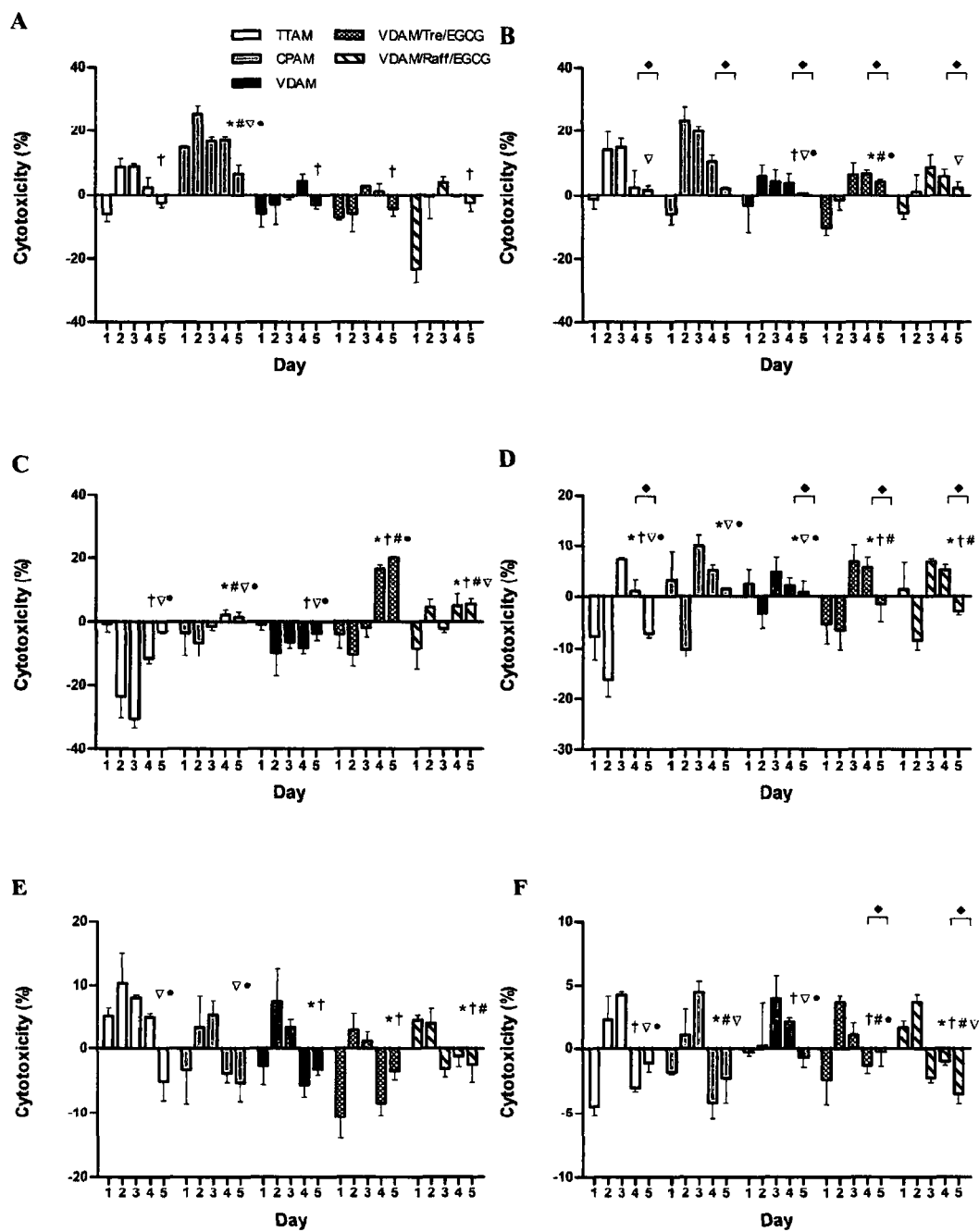
Figure 9:
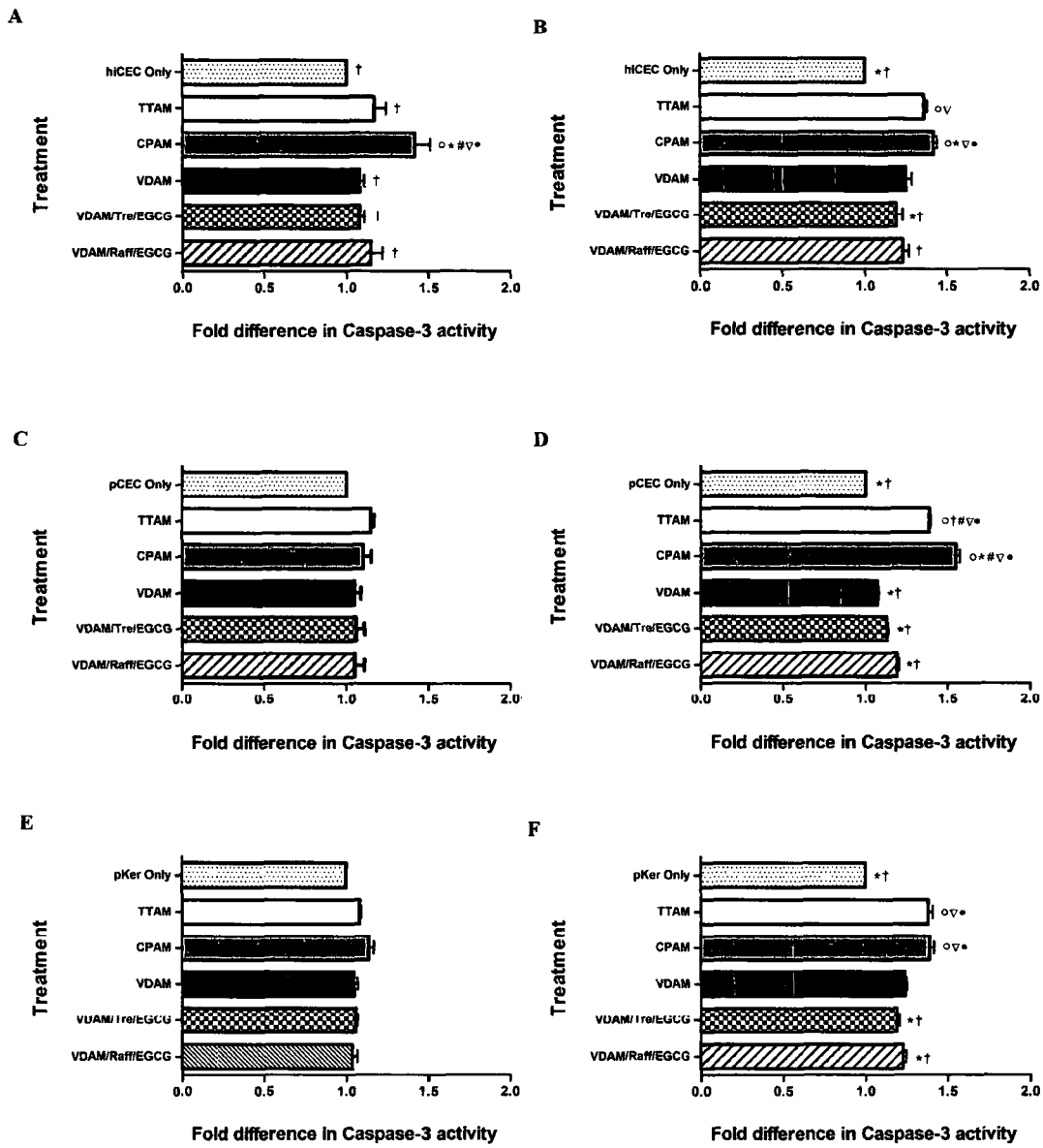
Figure 10:
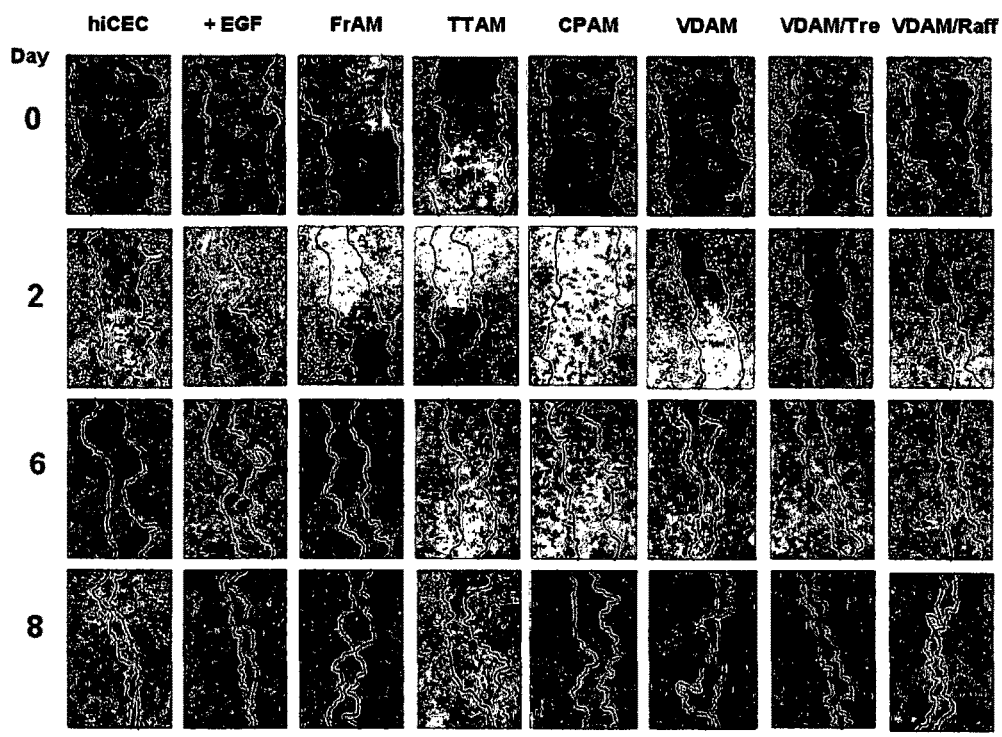
Figure 10:
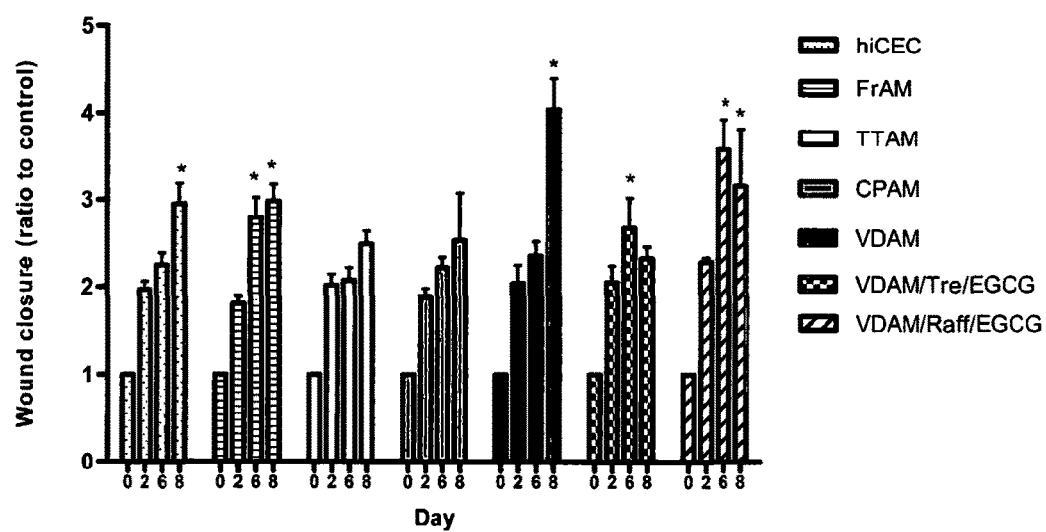
Figure 11:
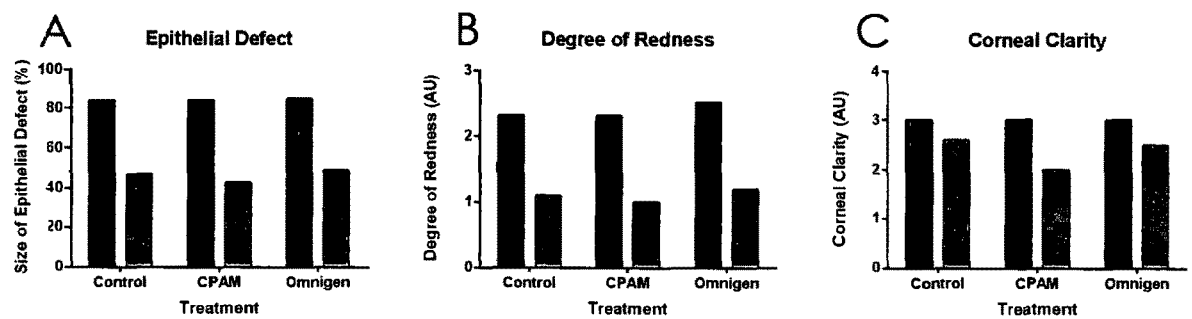
Figure 12:
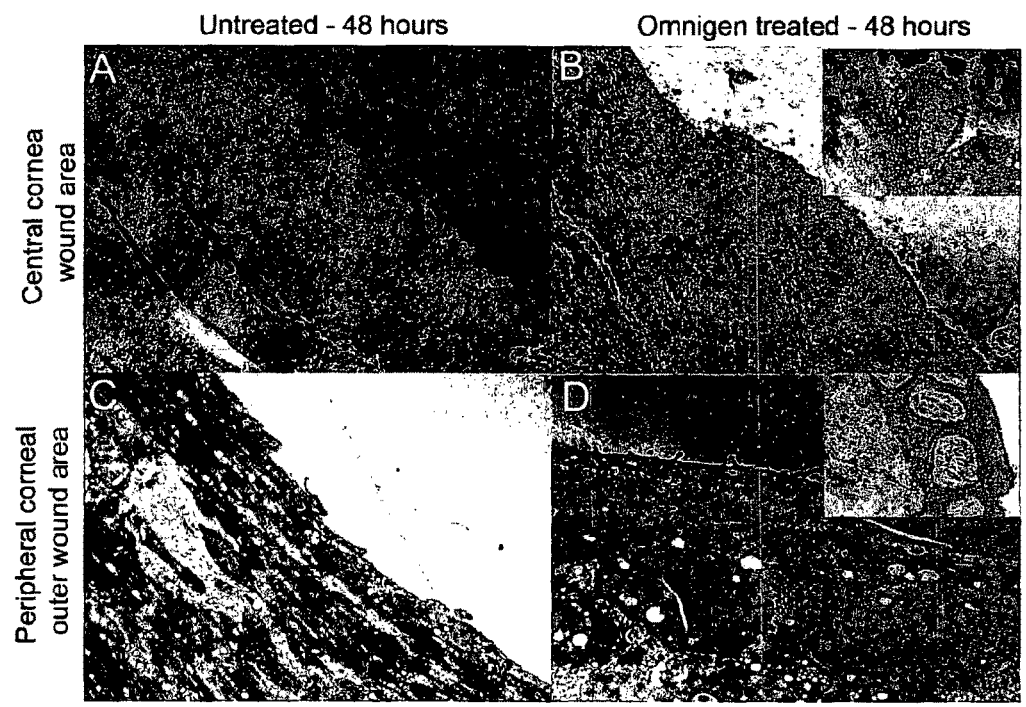
Figure 13:
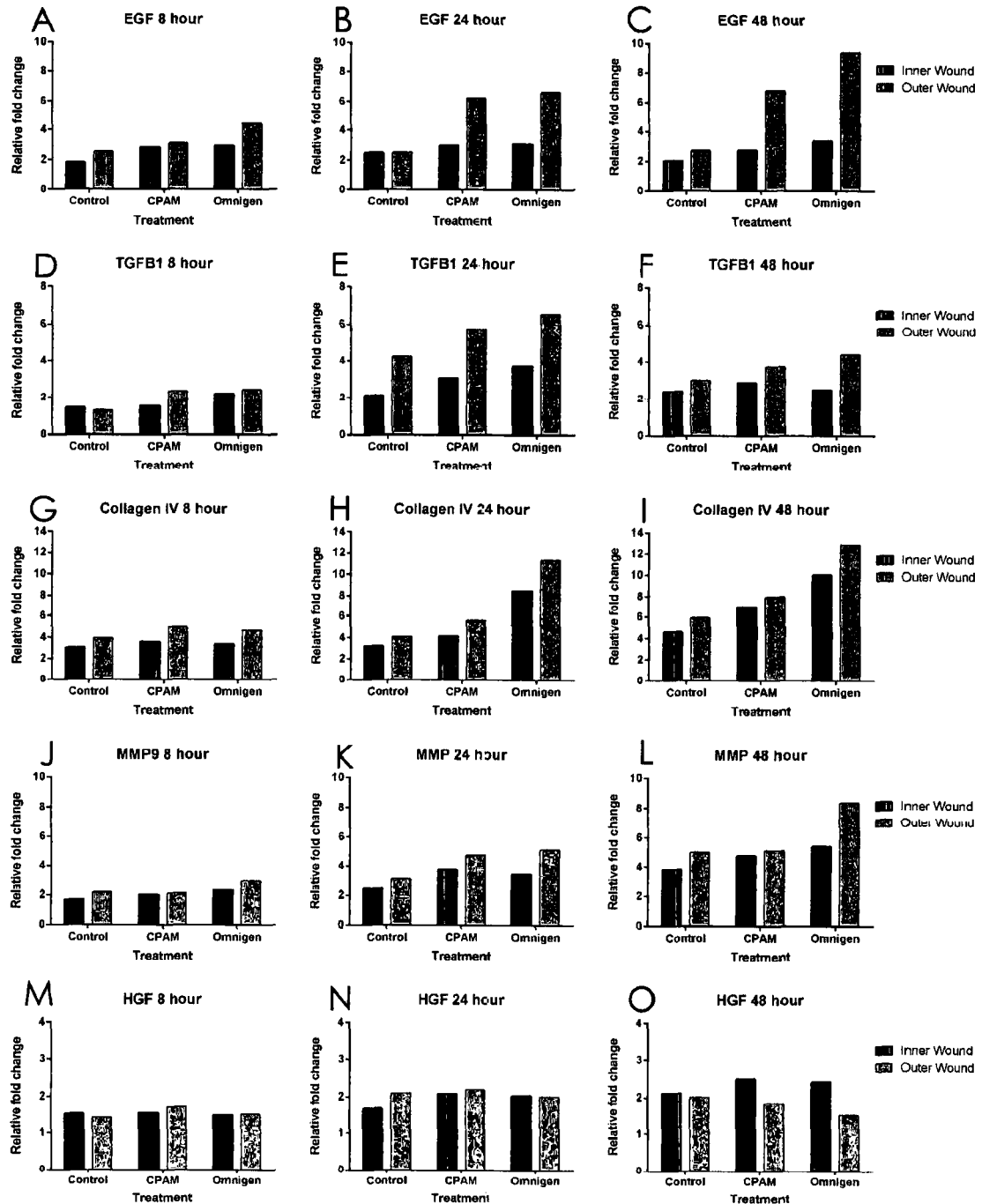
Figure 14:
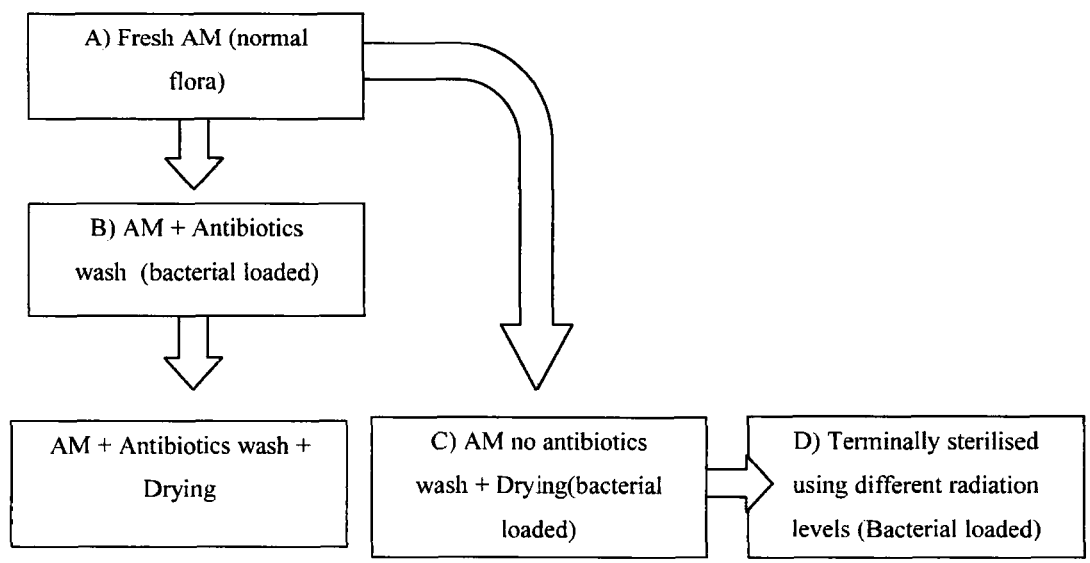
Figure 15:
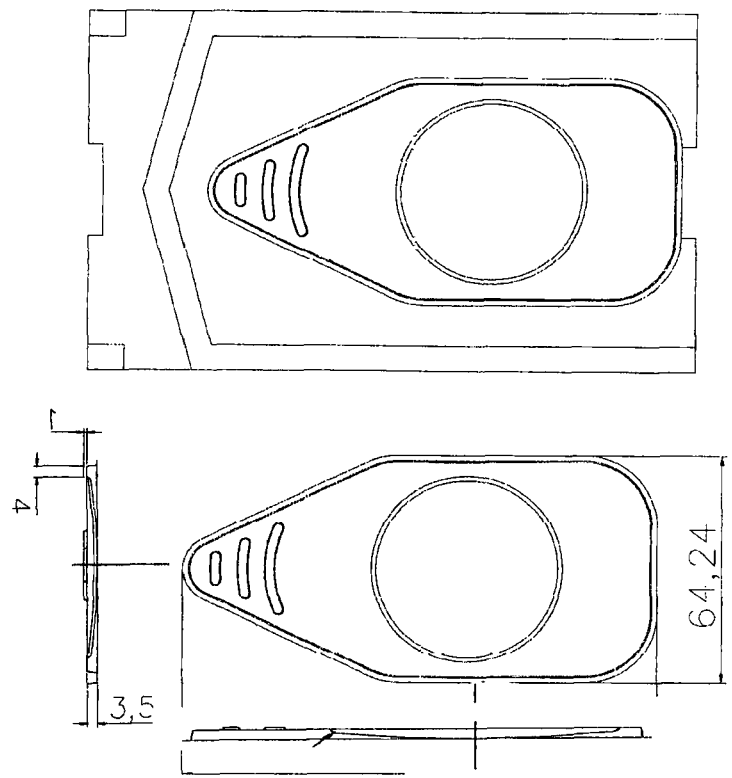
Figure 16:
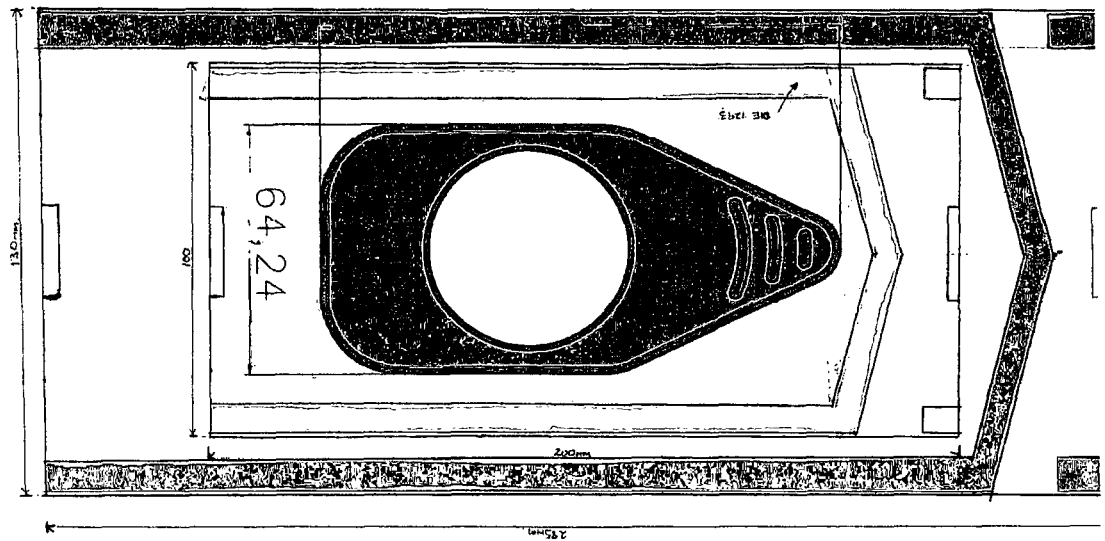
Figure 17:
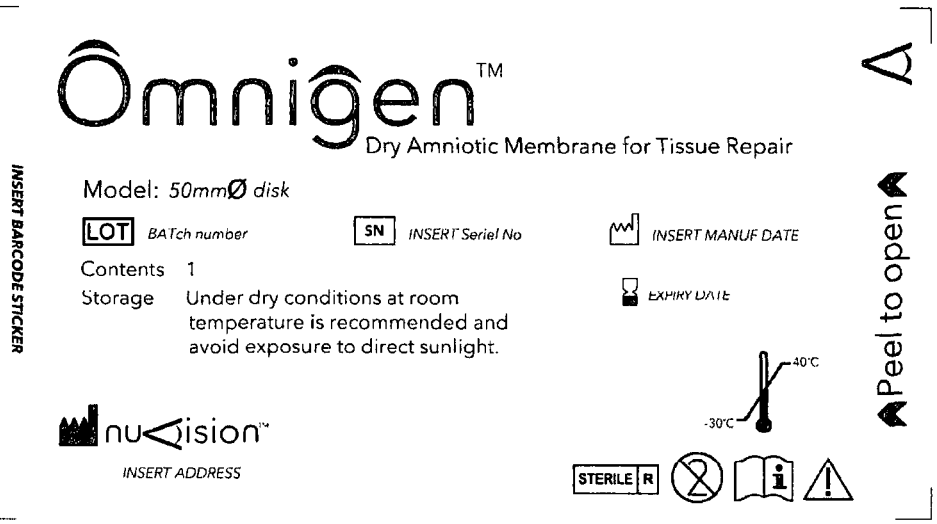
Figure 17:
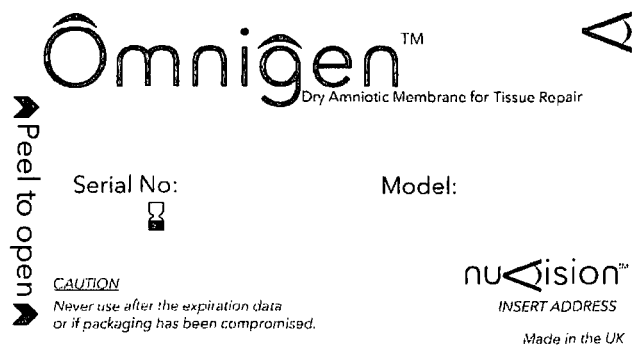
Figure 18:
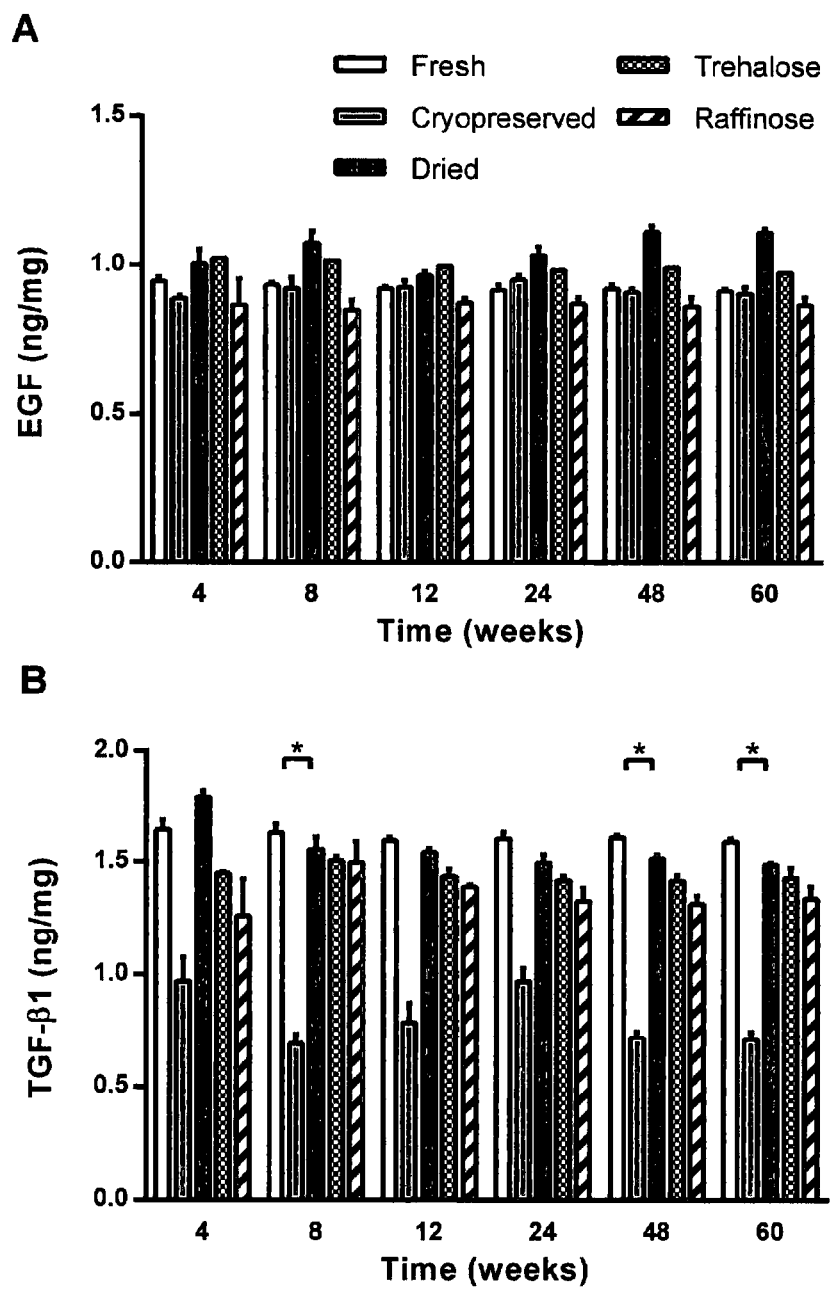
Figure 19:
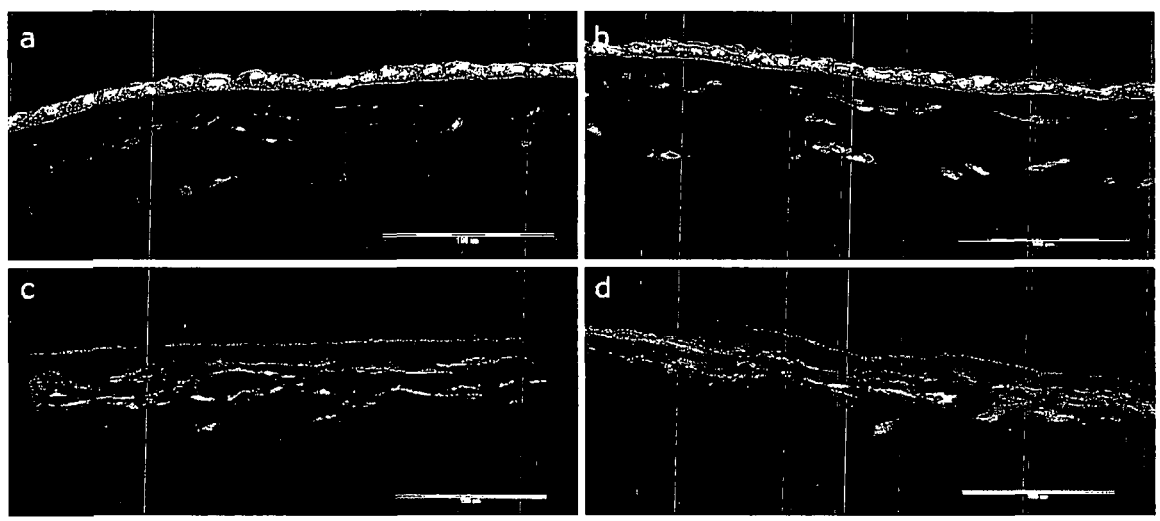

FIG. 3 shows concentrations of EGF (A) and TGF-β1 (B) protein, measured by ELISA in tissue that has been preserved using different techniques. Levels were measured cumulatively from 3×10 min washes in PBS and the protein extracted from the remaining tissue. Data are expressed as mean±SEM based on three separate experiments. *$p<0.05$ compared to FrAM, †$p<0.05$ compared to CPAM;

FIG. 4 shows a view of Representative immunofluorescence staining for (A) growth factors and biomarkers (B) cell adhesion, cytokine and angiogenesis markers (C) metalloproteases and (D) neurotrophic factors in fresh (FrAM), cryopreserved (CPAM), lyophilised (VDAM), lyophilised with lyoprotectants (VDAM/Tre/Raff) and thermolysin denuded (TTAM) AM, with functions potentially involved in ocular disease and epithelial wound healing. Amniotic cells nuclei were counterstained with DAPI (blue). Images shown are representative of triplicate experiments carried out on three membranes. Scale bar, 100 μm;

FIG. 5 shows different preserved preparations of AM were cultured over a 10-day period in PBS, using Scaffdex supports. Samples of PBS were taken at different time points and EGF (A) and TGF-β1 (B) levels were measured by ELISA. Data are expressed as mean±SEM based on three separate experiments. *$p<0.05$ compared to CPAM, †$p<0.05$ compared to VDAM/Raff/EGCG;

FIG. 6 shows Biochemical stability of EGF (A) and TGF-β1 (B) in optimised VDAM sections following extended storage periods of 4, 8, 12, 24, 48 and 60 weeks;

FIG. 7 shows Proliferation of corneal cells and keratocytes in direct and in-direct co-culture with differently preserved AM tissue was assessed using the WST-1 proliferation assay. (A) hiCEC in-direct, (B) hiCEC direct, (C) pCEC in-direct, (D) pCEC direct, (E) pKer in-direct and (F) pKer direct. Data are expressed as mean±SEM based on three separate experiments. *$p<0.05$ compared to TTAM, †$p<0.05$ compared to CPAM, # $p<0.05$ compared to VDAM, Δ$p<0.05$ compared to VDAM/Tre/EGCG and •$p<0.05$ compared to VDAM/Raff/EGCG, ♦$p<0.05$ compared to in-direct co-cultures at day 5;

FIG. 8 shows Cytotoxicity levels of differently preserved AM tissues in direct and in-direct co-culture with corneal cells and keratocytes were assessed by measuring lactate dehydrogenase (LDH) activity. (A) hiCEC in-direct, (B) hiCEC direct, (C) pCEC in-direct, (D) pCEC direct, (E) pKer in-direct and (F) pKer direct. Data are expressed as mean±SEM based on three separate experiments. *$p<0.05$ compared to TTAM, †$p<0.05$ compared to CPAM, # $p<0.05$ compared to VDAM, Δ$p<0.05$ compared to VDAM/Tre/EGCG and •$p<0.05$ compared to VDAM/Raff/EGCG, ♦$p<0.05$ compared to in-direct co-cultures at day 5;

FIG. 9 shows Apoptosis levels of differently preserved AM tissues in direct and in-direct co-culture with corneal cells and keratocytes were assessed by measuring caspase-3 activity post 5 days in culture. (A) hiCEC in-direct, (B) hiCEC direct, (C) pCEC in-direct, (D) pCEC direct, (E) pKer in-direct and (F) pKer direct. Data are expressed as mean±SEM based on three separate experiments. ° $p<0.05$ compared to hiCEC/pCEC or pKer only, *$p<0.05$ compared to TTAM, †$p<0.05$ compared to CPAM, # $p<0.05$ compared to VDAM, Δ$p<0.05$ compared to VDAM/Tre/EGCG and •$p<0.05$ compared to VDAM/Raff/EGCG, ♦$p<0.05$ compared to in-direct co-cultures at day 5;

FIG. 10 shows (A) micrographs showing cell migration and re-epithelialisation in the absence or presence of AM over an 8-day period. (B) Cell migration and wound closure rates were measured using Image J software. Area measurements were compared to control scratch wounds (day 0) and calculated as a ratio compared to control to assess wound closure in co-culture with differently prepared and preserved AM sections. Data are expressed as mean±SEM based on three separate experiments. *$p<0.05$ compared to corresponding time points in CPAM;

FIG. 11 shows the size of epithelial defect (A), degree of redness (B), and corneal clarity (C), pre (black) and post (grey) treatment in injured and untreated controls, following treatment with cryo-preserved AM (CPAM), or following Omnigen™ treatment;

FIG. 12 shows representative TEM images of in vivo chemically injured rabbit untreated (A, C) and treated with Omnigen™ (B, D), after 48 hour treatment. Images show central cornea wound (A-B) and peripheral corneal (limbal) wound area (C-D). Inlays show migrating;

FIG. 13 shows normalised gene expression of Rabbit EGF (A-C), TBFb1 (D-F), Collagen IV (G-I), MMP 9 (J-L), and HGF (M-O), in chemically burned eyes following no treatment (control), CPAM and Omnigen™ over 8 (A, D, G, J, M), 24 (B, E, H, K, N) and 48 (C, F, I, L, O) hours. Gene expression was assessed in central cornea (inner wound) and peripheral/limbal region (outer wound). For each samples replicates of 3 were performed;

FIG. 14 shows a schematic of the samples undergoing bioburden validation;

FIG. 15 shows schematic diagram of Omnigen™ inner holder tray;

FIG. 16 shows a schematic of Omnigen™ inner and outer pouch packaging with Omnigen™ holder inside;

FIG. 17 shows preliminary designs of Omnigen™ packaging labels;

FIG. 18 shows stability testing (ELISA) of EGF (A) and TGFb1 (B) protein contact (ng/mg) in amnion preserved by cryopreservation, freeze dried, Omnigen™ with trehlose, and Omnigen™ with rafinose, compared to fresh amniotic membrane; and FIG. 19 shows amniotic membrane denuding. Non-denuded AM (a and b) and AM denuded at 12 mins RT (c) and 37° C. (d).

FIG. 20 shows Table 3: SearchLight protein array data.

The biological properties of vacuum-dried AM (VDAM), and its biocompatibility as an ocular surface dressing were investigated, using cryopreserved amniotic membrane (CPAM) as a comparator. In addition the AM was also pre-treated with EGCG and either trehalose or raffinose to augment the tissue quality.

Dried amniotic membrane (AM) can be a useful therapeutic adjunct in ophthalmic surgery and possesses logistical advantages over standard cryopreserved AM. Differences in preservation techniques can significantly influence biochemical composition and physical properties of AM, potentially affecting clinical efficacy. Biochemical and structural effects of vacuum-drying AM were investigated in the absence and presence of saccharide lyoprotectants and its biocompatibility was compared to standard cryopreserved material. Methods: AM was cryopreserved (CPAM) or vacuum-dried (VDAM) with and without pre-treatment with trehalose (VDAM/EGCG/Tre) or raffinose (VDAM/EGCG/Raff) and the antioxidant EGCG. Structural and visual comparisons were assessed using electron microscopy. Localisation, expression and release of AM biological factors were determined using immunoassays and immunofluorescence. The biocompatibility of the AM preparations co-cultured with primary corneal epithelial cell (CEC) or keratocyte monolayers were assessed using cell proliferation, cytotoxicity, apoptosis and migration assays. Results: Vacuum-drying devitalised AM epithelium, but less so than cryopreservation, and cellular damage was reduced in VDAM pre-treated with trehalose or raffinose. VDAM alone, VDAM/EGCG/Tre and VDAM/EGCG/Raff showed greater factor retention efficiencies and bioavailability compared to CPAM and demonstrated a more sustained biochemical factor time release in vitro. Cellular health assays showed that VDAM and VDAM/Tre/Raff are compatible and superior substrates compared to CPAM for primary CEC expansion, with increased proliferation and reduced LDH and caspase-3 levels. This concept was supported by improved wound healing in an immortalised human CEC line (hiCEC) co-cultured with VDAM and VDAM/Tre/Raff membranes, compared to CPAM and fresh AM (FrAM).

Conclusions: This preservation process and the resultant optimised VDAM has enhanced structural properties and biochemical stability and is a superior substrate to conventional CPAM. In addition this product is stable and easily transportable allowing it to be globally wide reaching for use in clinical and military sectors.

Preservation of Amnion

Visual assessment of the different preserved AM, summarised in Table 2, revealed VDAM in the absence of a lyoprotectant produced a thin, furrowed and papery biomaterial. Rehydration produced a membrane akin in appearance to un-treated fresh AM material. Pre-treatment with the saccharide lyoprotectants produced a denser membrane with areas of residual sugar post vacuum-drying but retained its fresh-like visual and physical properties upon rehydration (Table 2). A glycerol pre-treatment produced a dry membrane appearance similar to VDAM alone but with increased brittleness and greasiness. Following rehydration membrane strength was restored, however the membrane remained more opaque compared to VDAM. Similar results were observed with DMSO rehydration, except that the membrane retained the translucency of fresh AM. Different TBA concentrations (10 and 40% v/v) were also tested at the pre-treatment stages. At 40% v/v some of the furrowing seen was reduced, but in general TBA gave a product that was very brittle following drying and very opaque on rehydration.

Sterile, freeze-dried AM can be prepared in the presence of complex saccharide lyoprotectants such as trehalose, a non-reducing disaccharide and a major energy source for some organisms during anhydrobiosis, a process that allows organisms to survive in extreme environments for indefinite periods. The precise mechanisms by which trehalose exerts its protective effects are multiple and not fully understood. Put simply, trehalose replaces intracellular water during dehydration or freezing to form a glassy matrix, thus preventing disruption of internal cell organelles. Trehalose is regarded as an exceptional lyoprotectant due to its high thermostability, a wide pH-stability range, high water retention capabilities, and its non-toxicity. It has been shown to protect pancreatic islet cells, platelets and red blood cells during freeze-drying, and it may also reduce corneal epithelial cell death during desiccation. Trehalose is also known as a stabiliser of proteins, for example maintaining the bioactivity and native-like structure of lyophilised insulin.

An alternative lyoprotectant, the trisaccharide raffinose accumulates in organelles during extreme exposure and acts as a free radical scavenger at high temperatures. A combination of raffinose and glutamine was shown to be effective in preserving sperm acrosomes, facilitating freezability. Both trehalose and raffinose have been shown to protect the integrity of red blood cell membranes following freezing, in the presence of dextran and glucose.

Epigallocatechin gallate (EGCG) is a potent anti-oxidant that has also been incorporated into cell and tissue lyoprotectant mixtures, promoting the viability of mononuclear cells and maintaining intact plasma membranes following freeze-thawing and freeze-drying.

TABLE 2

A summary of optimisation strategies employed and their impact on the visual and physical properties of VDAM

| | | VDAM | | Rehydrated VDAM | |
| --- | --- | --- | --- | --- | --- |
| Lyoprotectant | Conditions | Visual | Physical | Visual | Physical |
| Control (VDAM Only) | — | thin/furrowed/ papery | | ++++ translucent | ++++ |
| Glycerol 25% v/v | 4° C. | as control | | +++ opaque | ++++ |
| Glycerol 50% v/v | 4° C. | as control | | +++ opaque | +++ |
| DMSO 5% v/v | −80° C. | as control | | +++ translucent | +++ |
| DMSO 10% v/v | −80° C. | as control | | +++ translucent | +++ |
| TBA 10% v/v | RT | thinner/ uniform | | ++++ translucent | ++++ |
| TBA 40% v/v | RT | thinner/ less uniform | | +++ opaque | +++ |
| D-(+)-Trehalose 10% w/v | 2 h/37° C. | thinner/ dehydrated | | ++++ opaque | +++ |
| D-(+)-Trehalose 10% w/v + TBA 10% v/v | 2 h/37° C. | dense/powder residue | | ++++ translucent | ++++ |
| D-(+)-Raffinose 100 mM w/v | 2 h/37° C. | dense/powder residue | | ++++ translucent | ++++ |

TABLE 2-continued

A summary of optimisation strategies employed and their
impact on the visual and physical properties of VDAM

| Lyoprotectant | Conditions | VDAM Visual | VDAM Physical | Rehydrated VDAM Visual | Rehydrated VDAM Physical |
|---|---|---|---|---|---|
| As above + 1:10 Raffinose wash | 2 h/37° C. | reduced powder residue | ++++ | translucent | ++++ |

(Abbreviations: DMSO, dimethyl sulphoxide; TBA, tertiary butyl alcohol; RT, room temperature. All concentrations are represented as v/v excluding D-(+)-Raffinose w/v.)

Effects of Preservation Techniques on AM Structure

Figure 1:
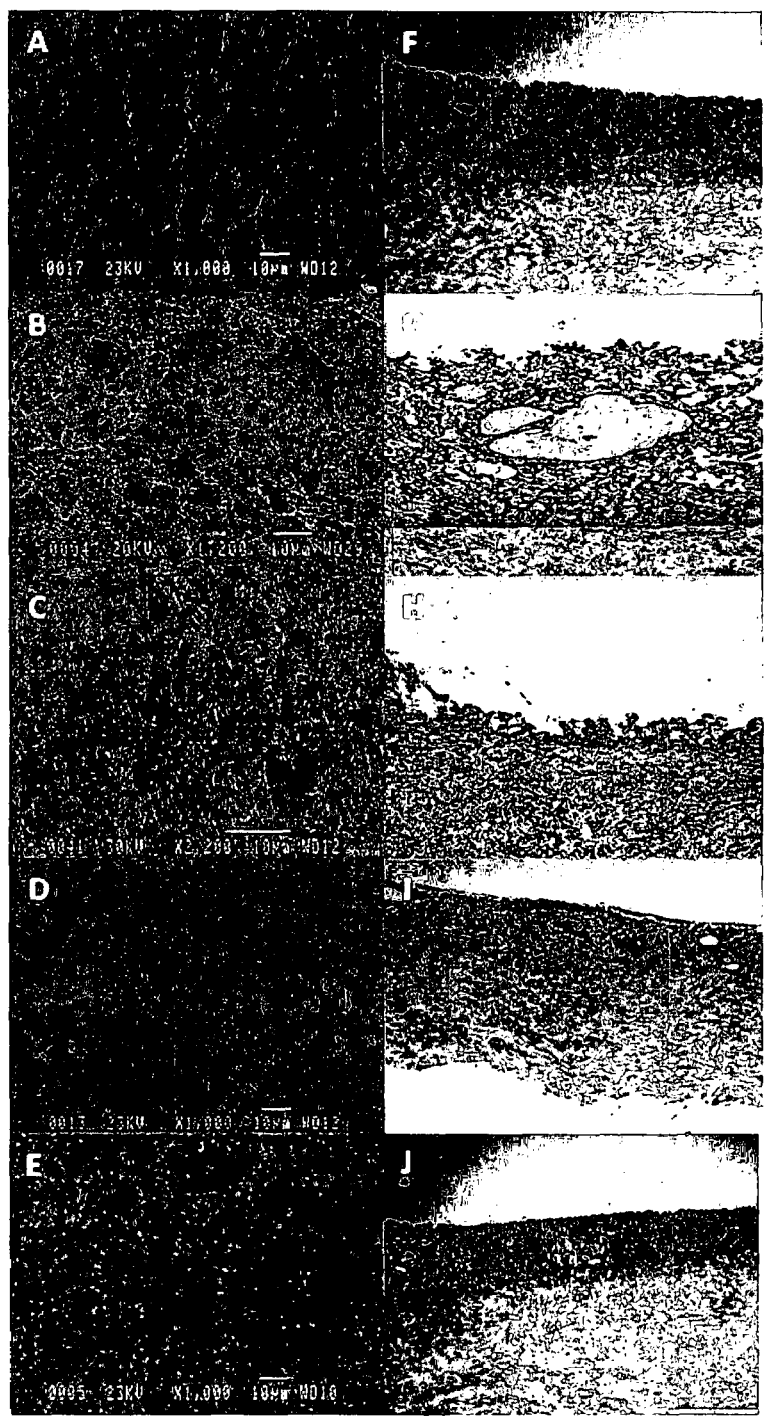
FIG. 1 shows SEM images of the epithelium of (A) FrAM (B) CPAM (C) TTAM (D) VDAM (E) VDAM Optimised and corresponding TEM images of (F) FrAM (G) CPAM (H) TTAM and (1) VDAM and (J) VDAM optimised substrates.

Following cryopreservation the typical amniotic epithelial cell (AEC) polygonal shape and cell patterns were lost. AEC appeared mainly intact but heavily damaged with clear fissures present between the cells with the damage and absence of surface microvilli. AEC had been clearly removed with denuding from the TTAM sample, exposing a uniform and consistent BM surface. In the VDAM sample AEC shape and pattern were more uniform but the cells were spherical and, non-polygonal and more compact. The appearance of AM following pre-treatment with trehalose was more FrAM like, with a more polygonal AEC structure and with limited surface and microvillus damage (FIG. 1).

The effects of optimised preservation on biochemical bioavailability

Figure 2:
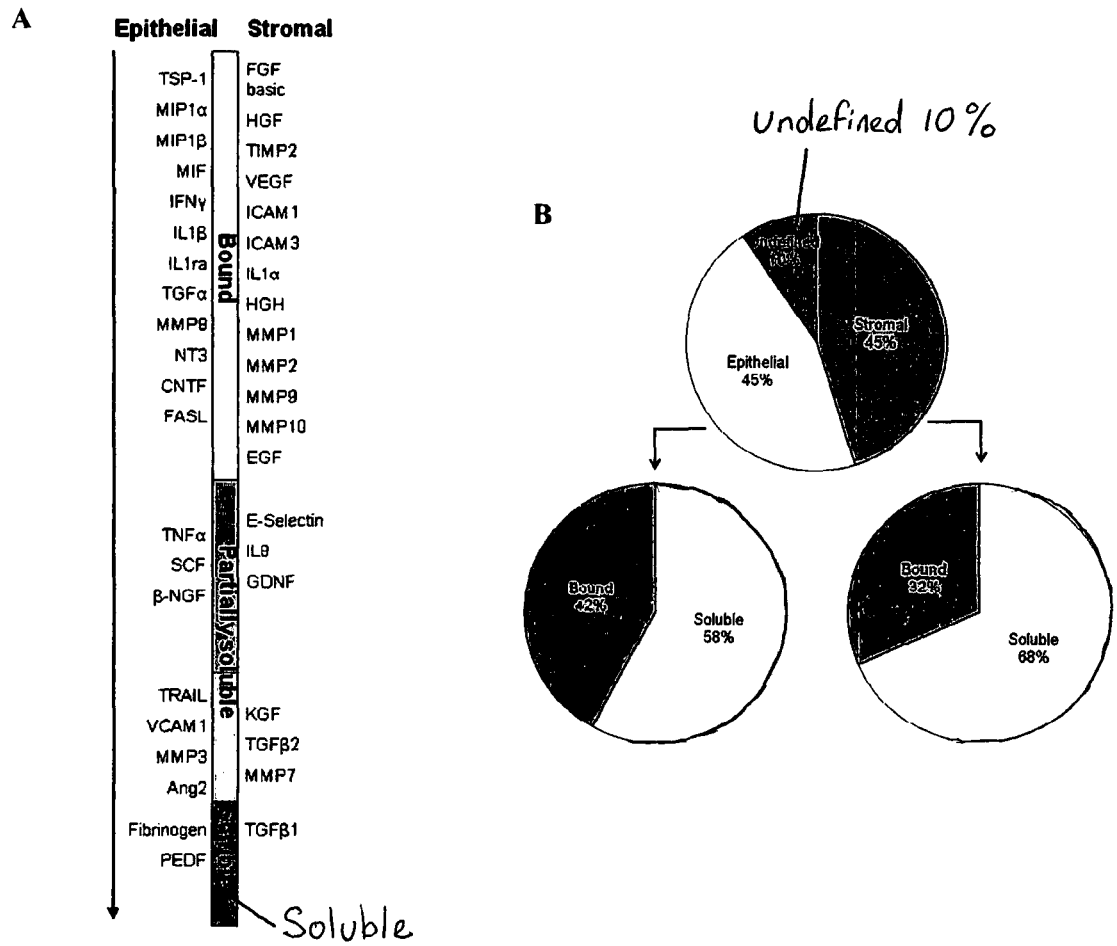
FIG. 2 shows (A) A schematic summary of the biochemical factors measured in amnion using SearchLight protein array technology, based on localisation and solubility. (B) The percentage of factors within each localisation (epithelial or stromal) and a percentage breakdown of soluble and in-soluble factors within these two cohorts.

To characterise the potential susceptibility of each factor to different preservation conditions, data from the SearchLight protein arrays (Table 3) was interpreted according to potential in situ localisation and solubility state. This generated 5 specific sub-divisions of cohorts; (i) epithelial factors that were predominantly soluble, reduced with epithelial damage and therefore susceptible to preservation related stripping and removed with denuding; (ii) epithelial, predominantly insoluble factors not reduced by preservation but removed with denuding; (iii) stromal factors that were partially soluble, reduced by preservation but not by denuding; (iv) stromal and predominantly insoluble factors not reduced by preservation and proportionately increased following denuding and (v) factors that were undefined and considered to be both epithelial and stromal (FIG. 2A). Of the 45 protein factors analysed (Table 3) there was an even divide between epithelial 45% (19/45) and stromal 45% (19/45)-related factors, with 10% (4/10) of factors undefined. Within the stromal cohort 68% (13/19) of factors were predominantly soluble and 32% (6/19) were bound and in-soluble. Analysis of the epithelial cohort showed that 58% (11/19) of factors were soluble and 44% (8/19) were bound (FIG. 2B).

Table 3. SearchLight protein array data. Each data value represents the average value of duplicate analysis on 3 separate biological donors. Abbreviations: TP, Total Protein; Ang2, Angiotensin 2; FGF, fibroblast growth factor; TIMP, tissue inhibitor of metalloproteases; VEGF, vascular endothelial growth factor; FASL, Fas ligand; TRAIL, tumour necrosis factor-related apoptosis-inducing ligand; VCAM, vascular cellular adhesion molecule; RANTES, regulated upon activation, normal T-cell expressed and secreted; MIP, macrophage inflammatory protein; MIF, macrophage migration inhibitory factor; IFN, interferon; TNF, tumour necrosis factor; HBEGF, heparin binding EGF-like growth factor; HGH, human growth hormone; SCF, stem cell factor; TGF, transforming growth factor; NGF, nerve growth factor; CNTF, ciliary neurotrophic factor; GDNF, glial cell-derived neurotrophic factor; NT3, neurotrophin 3.* significant decrease versus FrAM, † significant increase versus CPAM.

To validate the SearchLight data, and to explore in more detail factor retention efficiencies, ELISA and in situ localisation experiments were performed for EGF and TGF-$\beta$1 (FIG. 3). There was a significant reduction in both EGF and TGF-$\beta$1 factor retention in CPAM compared to FrAM, VDAM, VDAM/Tre/EGCG and VDAM/Raff/EGCG tissue. This pattern was most evident with the epithelial factor EGF, with CPAM retaining only 13% of total EGF overall and leaching 57% in the primary wash alone. Vacuum-drying alone and in the presence of trehalose or raffinose and the antioxidant EGCG retained EGF at efficiencies of 61, 88 and 83% respectively (Table 4A). The lyoprotectants provided greater factor retention and efficiencies similar to FrAM. This was also observed in corresponding TGF-$\beta$1 factor retention profiles with CPAM retaining 71% compared to FrAM (84%), VDAM (86%), VDAM/Tre/EGCG (93%) and VDAM/Raff/EGCG (92%) (Table 4B).

TABLE 4(A)

The effects of amnion preservation on EGF and (B) TGF-$\beta$1 factor retention.

| Preservation Treatment | Tissue Extract | Wash 1 | Wash 2 | Wash 3 | Cumulative Wash | Retention Efficiency (%) |
|---|---|---|---|---|---|---|
| | EGF (ng/mg total protein) | | | | | |
| FrAM | 0.977 ± 0.030 | 0.079 ± 0.011 | 0.057 ± 0.019 | 0.029 ± 0.003 | 0.165 ± 0.032 | 83 |
| CPAM | 0.540 ± 0.033 | 0.267 ± 0.007 | 0.140 ± 0.006 | 0.064 ± 0.011 | 0.471 ± 0.024* | 13 |
| VDAM | 0.695 ± 0.010 | 0.110 ± 0.008 | 0.103 ± 0.007 | 0.060 ± 0.014 | 0.273 ± 0.029† | 61 |
| VDAM/Tre/EGCG | 0.689 ± 0.082 | 0.044 ± 0.021 | 0.025 ± 0.010 | 0.017 ± 0.001 | 0.086 ± 0.032† | 88 |
| VDAM/Raff/EGCG | 0.759 ± 0.017 | 0.065 ± 0.005 | 0.044 ± 0.005 | 0.020 ± 0.010 | 0.129 ± 0.020† | 83 |
| | TGF-$\beta$1 (ng/mg total protein) | | | | | |
| FrAM | 1.773 ± 0.035 | 0.066 ± 0.004 | 0.025 ± 0.004 | 0.019 ± 0.003 | 0.110 ± 0.011 | 84 |
| CPAM | 1.251 ± 0.060 | 0.185 ± 0.014 | 0.103 ± 0.008 | 0.074 ± 0.004 | 0.362 ± 0.026* | 71 |
| VDAM | 1.587 ± 0.116 | 0.131 ± 0.009 | 0.062 ± 0.008 | 0.023 ± 0.003 | 0.216 ± 0.020† | 86 |
| VDAM/Tre/EGCG | 1.548 ± 0.068 | 0.049 ± 0.020 | 0.034 ± 0.009 | 0.030 ± 0.010 | 0.113 ± 0.039† | 93 |
| VDAM/Raff/EGCG | 1.368 ± 0.046 | 0.056 ± 0.007 | 0.038 ± 0.002 | 0.011 ± 0.004 | 0.105 ± 0.013† | 92 |

Data are expressed as mean ± SEM based on three separate experiments.
*$p < 0.05$ compared to FrAM, †$p < 0.05$ compared to CPAM For in situ validation, 13 protein markers were selected from the 5 different factor cohorts described earlier and with functions potentially involved in ocular disease and epithelial wound healing (FIG. 4). The collective pattern in staining demonstrated a decrease in protein detection in 77% (10/13) of markers in CPAM, compared to FrAM (Table 5). The exceptions were the matrix metalloproteases (MMP)-2, MMP-3, MMP-9 and brain derived neurotrophic factor (BDNF), where staining intensities remained constant across the different preservation techniques as they were stromal in origin and mostly insoluble. Interestingly, staining for predominantly stromal-derived markers e.g. Pigment epithelium-derived factor (PEDF), MMP-2 and intercellular adhesion molecule (ICAM)-1, appeared more intense around the keratocytes (FIG. 4). In VDAM, protein detection was comparable to FrAM in 69% (9/13) of markers assessed, while comparable detection in VDAM/Tre/EGCG was 85% (11/13) (FIG. 4 and Table 5).

TABLE 5

A summary of the immunofluorescent staining intensities for each biochemical factor investigated at the protein level.

| Factor | Function | Type | FrAM | CPAM | VDAM | VDAM/Tre/Raff |
|---|---|---|---|---|---|---|
| KGF | Angiogenesis | Epithelial | +++ | ++ | +++ | +++ |
| PEDF | Biomarker | Stromal | +++ | ++ | ++ | +++ |
| TSP-1 | Biomarker | Epithelial | +++ | ++ | +++ | +++ |
| E-Selectin | Cell Adhesion | Epithelial | +++ | ++ | +++ | +++ |
| ICAM-1 | Cell Adhesion | Stromal | +++ | ++ | +++ | +++ |
| IL-8 | Cytokine | Epithelial | +++ | ++ | ++ | +++ |
| EGF | Growth Factor | Epithelial | ++ | ++ | ++ | +++ |
| TGF-β1 | Growth Factor | Epithelial/Stromal | +++ | ++ | +++ | ++ |
| MMP-2 | Metalloprotease | Epithelial/Stromal | +++ | +++ | +++ | ++ |
| MMP-3 | Metalloprotease | Epithelial/Stromal | +++ | +++ | +++ | +++ |
| MMP-9 | Metalloprotease | Stromal | +++ | ++ | +++ | +++ |
| BDNF | Neurotrophic Factor | Stromal | ++ | +++ | ++ | +++ |
| β-NGF | Neurotrophic Factor | Epithelial/cellular | +++ | ++ | +++ | +++ |

3+, intense expression; 2+, moderate expression; 1+, faint expression; −, negligible expression In situ protein expression data supported SearchLight protein array data analysis demonstrating a significant decrease in protein expression in CPAM, particularly in any epithelial-derived and soluble protein. However the vacuum-drying process and in the presence of raffinose this protein loss was prevented, retaining beneficial factors more effectively, with little or no loss (Table 5 and FIG. 4).

Biochemical Factor Time Release

Time release studies showed that there was an immediate and time dependent release of EGF and TGF-β1 in culture, over a 10 day period (FIG. 5). The EGF profile showed a sudden increase in EGF release from CPAM at day 4 (6.07±0.04 ng/ml) and this then decreased over time. EGF release from VDAM/Tre/EGCG and VDAM/Raff/EGCG demonstrated a more sustained release over time with levels ranging from 1.36-3.83 ng/ml and 1.03-2.61 ng/ml respectively (FIG. 5A) TGF-β1 profiles showed a sustained time release from CPAM and VDAM/Tre/EGCG with levels peaking at 1.52±0.60 ng/ml and 1.77±0.42 ng/ml at day 10. However TGF-β1 release from VDAM/Raff/EGCG peaked (2.36±0.73 ng/ml) at day 2 and then decreased over the following 6 days (FIG. 5B).

Biochemical Stability of Amnion Following Preservation and Storage

To investigate the stability of factors over long term storage, the levels of two significant wound healing factors were assessed sequentially over a period of 15 months. No significant changes in EGF concentration were observed in tissue following preservation and between storage periods of 4, 8 or 12 weeks. TGF-β1 concentrations appeared to vary between samples, illustrating biological variation, but the results suggested no TGF-β1 degradation occurred over the 12 weeks of storage (FIG. 6).

The Effect of Different Amniotic Membrane Preparations on Human Corneal Epithelial Cell and Keratocyte Proliferation Indirect co-culture of CPAM with hiCEC induced a stable decrease in proliferation over the 5 day culture period (FIG. 7A), compared to cells cultured without AM. Similarly poor proliferation rates were also observed when pCEC were used (FIG. 7C). Although denuded (TTAM) and VDAM induced a dramatic initial drop in proliferation in the initial 48 hour period in both hiCEC and pCEC, a dramatic increase in proliferation was observed with proliferation rates of 17% and 9% in hiCEC and 14 and 17% in pCEC at day 4. In contrast, VDAM/Tre/EGCG and VDAM/Raff/EGCG consistently promoted proliferation over the entire culture period, and at comparable rates, with levels peaking at 18 and 16% in hiCEC at day 4 and 27 and 29% in pCEC at day 5 (FIGS. 7A and C).

Direct co-culture promoted a greater and comparable increase in proliferation in both hiCEC and pCEC using VDAM, VDAM/Tre/EGCG and VDAM/Raff/EGCG, compared to in-direct culture (FIGS. 7B and C). This effect was more pronounced in pCEC with the highest rates in VDAM/Tre/EGCG and VDAM/Raff/EGCG, levels reaching 21-36% at day 3 (FIG. 7D). Although direct co-culture also improved proliferation rates of hiCEC with CPAM, proliferation was not improved in pCEC compared to hiCEC. While indirect culture with TTAM marginally increased hiCEC and to a greater extent pCEC proliferation rates after day 3, direct culture of both cell types with TTAM induced a considerable negative proliferative effect.

The effect of co-culture on primary keratocyte (pKer) proliferation was also tested in a similar manor. Indirect co-culture showed a progressive increase in proliferation in the presence of VDAM, VDAM/Tre/EGCG and VDAM/Raff/EGCG compared to CPAM, with the optimised VDAM/Tre/EGCG and VDAM/Raff/EGCG performing the best. Increasingly negative proliferation rates were observed with TTAM (FIG. 7E). Conversely, direct culture of pKer with all membrane preparations resulted in a considerable negative effect on proliferation, supporting the evidence AM inhibits pKer growth. The negative growth effect was sustained in TTAM and CPAM, but was overpowered in VDAM membranes most likely due to a greater retention of growth factors (FIG. 7F), though proliferation was reduced (18% for any time point) compared to indirect pKer culture.

The Cytotoxic Effect of Different Amniotic Membrane Preparations on Human Corneal Epithelial Cells and Keratocytes Indirect co-culture of cells with VDAM and derivatives demonstrated generally reduced cell death in both hiCEC and pCEC (FIGS. 8A and C) which corroborates and increase in proliferation (FIGS. 7A and C). CPAM, and to a lesser degree TTAM, exerted a greater cytotoxic effect in hiCEC with levels reaching 20% and 8% at day 2, respectively. This supports the poor proliferation and therefore poor cellular health of hiCEC when cultured in CPAM and TTAM. Interestingly, cytotoxicity was greatly reduced in pCEC with TTAM suggesting pCEC are less sensitive to cytotoxicity, which was therefore epithelial in origin and was removed during denuding.

Direct co-culture of all samples types, including EGF without AM, showed a moderate increase in cytotoxicity after the first (hiCEC) and second (pCEC) day, with the greatest cytotoxicity in CPAM and least in VDAM derivatives (FIGS. 8B and D). The increase in cytotoxicity was greater and more evident with hiCEC in direct culture compared to in-direct. The cytotoxic effect of direct culture with VDAM peaked at no more than 10%, decreasing following day 3 (FIG. 8D) and levels were comparable with EGF controls.

Cytotoxicity in direct cultures of both cell types appeared to follow a pattern, which is most clearly seen in hiCEC, in that following an initial reduced cytotoxicity on the first day (first two days and at a greater deduction for pCEC) a sharp increase in cytotoxicity appeared to consistently occur on day 3 which then decreased over the remaining culture period (FIGS. 8B and D). This pattern was also similar but more pronounced when pKer were cultured with the various AM preparations. For direct culture of pKer, levels did not exceed 10% and decreased to nominal levels post 3 days in culture. Co-culture with TTAM showed the most pronounced cytotoxic effect at day 2 (FIG. 8E). Direct co-cultures with AM preparations showed similar cytotoxic profiles to in-direct culture with cytotoxicity decreasing over the 5 day culture period and levels did not exceed 4% (FIG. 8F).

The Apoptotic Effect of Different Amniotic Membrane Preparations on Human Corneal Epithelial Cells and Keratocytes Having demonstrated varying cell growth and death rates in pCEC and pKer on different AM preparations, the role of apoptosis was investigated using the apoptosis marker caspase-3 expression as an indicator. In-direct and direct co-culture of the vacuum-dried preparations with pCEC or pKer promoted no significant increases in caspase-3 activity compared to cell only controls. However CPAM significantly ($p<0.05$) increased caspase-3 activity when directly cultured with hiCEC (0.4 fold), pCEC (0.6) and pKER (0.4) and in-directly cultured hiCEC, compared to cells alone, following five days in culture. This suggests CPAM, which is comparable to conventional intact AM, induces cell death through apoptosis. Although some increases in caspase-3 activity were observed for the remaining cell/substrate co-cultures, these were non-significant (FIGS. 9A-F). Similarly, TTAM significantly ($p<0.05$) increased caspase-3 activity compared to control, when directly cultured with hiCEC (0.4 fold), pCEC (0.4 fold) and pKER (0.4 fold).

Wound Healing

To evaluate the effects of different AM preservation conditions on re-epithelialisation following injury, scratch wound healing assays were performed and wound closure rates calculated at days 2, 6 and 8 compared to control (day 0) and in the presence of hiCEC in-directly cultured with the different AM preparations (FIGS. 10A and B). Results showed that although all samples demonstrated wound healing up to 8 days and beyond, FrAM, TTAM, and CPAM showed no improvement over hiCEC alone (no amnion control). VDAM and VDAM/Raff/EGCG significantly improved wound healing compared to hiCEC (4-fold $p<0.05$) and CPAM (3.2-fold $p<0.05$) at day six and eight. VDAM/Tre/EGCG did not promote significant re-epithelialisation compared to control cultures without amnion.

DISCUSSION

In recent years freeze-dried AM has become an alternative to CPAM as a substrate for stem cell expansion and as a conjunctival replacement in pterygium surgery. In addition dried AM preparations, cross-linked with glutaraldehyde, have been used as a primary treatment for corneal perforations, indicating its increased usefulness over CPAM in certain clinical situations. This may reflect easier surgical handling of the dried tissue, which can be glued rather than sutured onto the ocular surface. Evidence suggests that dried AM may be advantageous in a number of clinical conditions, for instance as an inlay graft for persistent epithelial defects or as a patch for the entire ocular surface in acute burns. Animal model studies have indicated that freeze-dried AM is at least as effective as CPAM as a substrate for ocular surface reconstruction. Besides offering clinical advantages, dried AM eliminates the need for temperature-controlled and monitored storage transportation, significantly reducing expenditure.

To minimise the effects of freeze damage, we pre-treated AM with lyoprotectants prior to vacuum-drying. SEM images show that while cryopreservation and vacuum-drying without lyoprotectants are highly destructive to cellular integrity, our optimised VDAM preparations exhibited less visible structural damage and appear structurally akin to FrAM. In FrAM preparations, the polygonal AEC are closely apposed to each other and the microvillous surface retains a healthy appearance. In comparison, AEC on the surface of VDAM prepared with no lyoprotection showed evidence of collapse, and the microvilli appeared sparse and flattened. The overall structure was better retained with lyoprotectants. This was supported by TEM images showing that VDAM without pre-treatment had a more condensed collagen network, and the stromal and epithelial layers appeared thinner following the vacuum-drying process. In comparison, CPAM exhibited extensive intracellular vacuole formation and signs of cell death. While the visual quality of reconstituted lyophilised AM has been reported to be poor in comparison to FrAM and CPAM, our studies found no obvious differences in quality. We attribute these findings to pre-treatment of the AM with a saccharide lyoprotectant and the elimination of a pre-freeze step allowing preservation of cellular and matriceal integrity.

In addition to the structural differences observed, the study confirmed that all preservation methods resulted in the loss of biological factors from AM. The loss of factors was greatest in CPAM with levels of loss of 58% of the factors analysed compared to only 35% in VDAM/Tre/EGCG and VDAM/Raff/EGCG. Lyoprotected VDAM showed increased factor retention in 29 out of 45 of the number of factors analysed when compared to CPAM. Standardised vacuum-drying and in combination with trehalose or raffinose are therefore superfluous to cryopreservation for retaining the biochemical profile of AM. This contradicts previous research findings suggesting diminished growth factor levels in lyophilised AM compared to CPAM. However, this may be attributed to the treatment of these membranes with γ-irradiation, which is known to result in structural damage and may cause a further decrease in protein levels.

In 2009, Rodriguez-Ares and colleagues published similar results to ours. They analysed the biochemical profiles of AM preparations, finding that the levels of biochemical factors associated with wound healing were decreased in lyophilised AM compared to CPAM, but these were not significant. The biochemical profile of our optimised VDAM returned a 76% increase in factor retention compared to CPAM, and a 32% increase compared to non-lyoprotected VDAM. This demonstrates that trehalose and raffinose stabilise the tissue, enabling a more physiological biomaterial to be produced. In the future this may contribute to improved clinical outcomes.

Differences in preservation methods do not solely explain the variation in AM factor levels, which may also be influenced by gestational age, donor age, differences in handling techniques and the location of the sample's origin within the donor tissue. However, our immunofluorescence data confirm our finding that lyoprotection of AM with trehalose or raffinose prevents loss of soluble biological factors. The levels of keratinocyte growth factor (KGF), PEDF, E-Selectin, ICAM-1 and β-nerve growth factor (NGF) diminish following cryopreservation, as denoted by the reduced staining intensity, but are highly expressed in VDAM and VDAM/Tre/EGCG and VDAM/Raff/EGCG. This is consistent with the protein array data. In contrast, an immunohistochemical analysis of AM extracellular matrix molecules has indicated reduced intensity following drying compared to cryopreservation. This may be attributed to radiation damage.

Assuming that the retention of key growth factors in AM preparations is germane to its effectiveness in some clinical situations, the rate of release of these factors may also be significant. Ideally, AM would secrete its factors over a prolonged period and not its whole reserve instantaneously. Our assays show that as well as improved factor retention, the release of EGF from optimised VDAM was more sustained than CPAM over a 10 day period suggesting that the immediate release from CPAM was attributable to the freeze-thaw damage. This indicates that optimised vacuum-dried AM will have both increased factor content and prolonged release potentially improving the overall clinical effectiveness of AM over CPAM.

Cellular health assays supported this showing optimised VDAM substrates promote significant increases in corneal epithelial and keratocyte proliferation, with reduced overall cytotoxicity and apoptosis levels, compared to TTAM and CPAM in both direct and indirect cultures. Similarities between CPAM and TTAM further suggest that this phenomenon is explained by the removal of essential cell-based growth factors essential for promoting wound healing, rather than as a result of vacuum drying per se.

The proliferation rates of cells grown on TTAM and CPAM substrates were similar. Keratocytes cultured on TTAM substrates were slower to proliferate, suggesting that epithelial factors also play a role in keratocyte proliferation. The proliferation of hiCEC was increased in the presence of all substrates compared to pCEC cultures, possibly reflecting the robustness of these immortalised cells in comparison to pCEC.

Increased wound closure rates were observed in hiCEC co-cultures with the optimised VDAM substrates compared to CPAM and even FrAM. This may be attributed to the bioavailability of wound healing factors e.g. EGF, HGF, PDGF and TGF-β retained in the tissue by our optimised preservation technique.

In this study, it has been shown that the saccharide lyoprotectants trehalose and raffinose improve the quality of VDAM by maintaining its structural and biochemical properties over extended periods. This implies its improved stability as an ocular surface dressing that can be stored and transported without the need for freezing, reducing costs and allowing it to be used outside modern hospital settings. In the absence of availability of optimised drying procedures our work indirectly supports the use of denuded AM, using an optimised procedure is more effective than conventional intact CPAM.

Materials and Methods

Tissue Procurement and Preparation

The following research was carried out with the approval of the local research ethics committee and the study complied with the tenets of the Declaration of Helsinki. 12 human placental samples were collected from consenting patients undergoing elective caesarian section and prepared according to previously published methodology. Patients with a history of antenatal problems e.g. gestational diabetes or placenta praevia were excluded from the study. In brief, excess blood was washed away with a balanced salt solution and the amnion was separated from the placenta and the chorion. The amnion was further washed for 3×15 minutes to allow the spongy layer to expand for easy removal. Mid-region sections were preserved and then circular sections were prepared using a 5 cm 0 trephine. Sections were used immediately or placed in vacuum pouches prior to drying and vacuum sealing.

Tissue Preservation and Optimisation

Processed AM segments from 12 donors were either used fresh (FrAM) or were prepared and preserved using one of five methodologies to produce; cryopreserved AM (CPAM), thermolysin treated vacuum-dried AM (TTAM), vacuum-dried AM (VDAM), and vacuum-dried post incubation with epigallocatechin (EGCG, 1 mg/mL, Sigma-Aldrich, UK) and the lyoprotectants trehalose (VDAM/Tre/EGCG) or raffinose (VDAM/Raff/EGCG). CPAM: AM segments were preserved in sterile Dulbecco's phosphate buffered saline (DPBS, Sigma-Aldrich) in 20 mL sterile tubes, at −80° C., using established methodologies within our department. VDAM: FrAM segments were uniformly spread out, epithelial side up, in vacuum pouches. This was then double heat sealed on three sides prior to drying. Drying was performed using an Alpha 1-4 LSC freeze-dryer (Christ, Germany). Following a prechilling cycle to −45° C., the cycle comprised of a main dry phase for 1 hour (shelf temperature 15° C., vacuum pressure 1.030 mbar, safety pressure 1.650 mbar) followed by a final drying phase for 30 minutes (shelf temperature 20° C., vacuum pressure 0.0010 mbar, safety pressure 1.650 mbar). Following completion of the drying cycle the bag was heat sealed under vacuum using a Multiple 315 vacuum packaging chamber, (Orved, Italy) and stored at room temperature, and away from direct light, until further analysis. TTAM: FrAM segments were denuded of epithelium with thermolysin (Sigma-Aldrich, 125 μg/mL in PBS) according to our published methodologies[Hopkinson, A., et al., Tissue Eng Part C Methods, 2008. 14(4): p. 371-81]. Treated membranes were then dried as per VDAM. VDAM/Tre/EGCG or VDAM/Raff/EGCG: To optimise the vacuum-drying procedure, prior to vacuum-drying, AM segments were uniformly spread out in Petri dishes and bathed in a series of solutions containing glycerol/PBS (ratios of 1:4 and 1:2), DMSO (Sigma-Aldrich)/PBS (5 and 10% v/v), and tertiary butyl alcohol (TBA, Sigma-Aldrich)/PBS (10 and 40% v/v) for 10 minutes each. Alternatively segments were incubated with 2, 10, and 25% w/v D-(+)-Trehalose dihydrate (Acros Organics, Belgium) in PBS or 25, 100 and 200 mM w/v D-(+)-Raffinose pentahydrate (Acros Organics), and EGCG (1 mg/mL, Sigma-Aldrich) for 2 hours at 37° C. Additionally segments were treated with 10% w/v D-(+)-Trehalose dihydrate, 10% v/v TBA and EGCG (1 mg/mL). Prior to vacuum-drying membrane sections were washed briefly in a 1:10 dilution of the original saccharide lyoprotectant to remove excess residue from the surface. The precise parameters for producing VDAM/Tre/EGCG or VDAM/Raff/EGCG were 10% w/v D-(+)-Trehalose dihydrate or 100 mM D-(+)-Raffinose pentahydrate, co-incubated with EGCG (1 mg/mL).

Optimum Rehydration Assay

Different volumes of PBS (0.5, 0.75 and 1.0 mL) were applied to separate circular sections (5 cm Ø) of VDAM/Raff/EGCG and allowed to rehydrate for 5 minutes. Samples were visually inspected and assessed based upon the percentage of tissue rehydrated and the level of residual fluid remaining.

Visual and Strength Assessment

Triplicate 5×5 cm2 samples from 6 donor membranes were bathed briefly in the solutions outlined and vacuum-dried prior to visual appearance and strength assessment. Preserved membranes were visually compared to a control piece of vacuum-dried AM. Membranes were graded according to a 4 point scale with control material being assigned the maximum of 4 for strength and visual clarity; this was carried out by two separate investigators. Following assessment, membranes were rehydrated with a pre-optimised volume of 1 mL of sterile DPBS for 10 minutes, and the visual appearance and strength were compared to the control, using the assessment described above.

Electron Microscopy (EM)

Scanning EM (SEM) and transmission EM (TEM) studies were performed on membranes from 3 individual donors, prepared in duplicate for each of the 6 sample preservation types. For each sample, 1 cm diameter discs of preserved AM samples were overlaid on corresponding discs of polyvinylidene fluoride (PVDF) membrane (epithelial side up) and processed for SEM and TEM according to previously published methodologies[Hopkinson, A., et al., Optimization of amniotic membrane (AM) denuding for tissue engineering. Tissue Eng Part C Methods, 2008. 14(4): p. 371-81]. SEM samples were observed in a JEOL 840 microscope (JEOL, UK) and appropriate digital images were recorded using an integrated Iscan digital imaging system. A JEOL 1010 microscope was used to observe the TEM sections at 100 kV, and recorded using an SIS integrated digital camera system.

Biochemical Analysis

Soluble proteins were extracted from segments of FrAM, CPAM, TTAM, VDAM, VDAM/Tre/EGCG or VDAM/Raff/EGCG from 3 AM donors. Samples were ground under liquid nitrogen and reconstituted in 1× Tris buffered saline+ 0.05% v/v Triton-X (Sigma-Aldrich) (TBSTX) buffer for 20 minutes at room temperature. Insoluble material was removed by centrifuging at 20,000×g, for 15 minutes, at 4° C. and the protein concentration of each supernatant was determined using a 2D Quant kit (GE Healthcare, UK). Protein arrays were carried out in duplicate using SearchLight immunoassay technology (Aushon Biosystems) for a profile of 48 protein analytes, including angiogenesis factors, biomarkers, cell adhesion molecules, chemokines, cytokines, growth factors, matrix metalloproteinases and neurotrophic factors (see Table 3). Analytes failing to provide a data value were omitted from the study and remaining data normalised according to ng/mg of protein extract.

ELISA

Reconstituted AM segments (5 cm Ø) for all treatments from 3 donors were washed in 5 mL saline containing protease inhibitors (complete protease inhibitor tablets; Roche, UK) for 10 minutes each wash. CPAM storage medium and washes were concentrated and retained for analysis. Samples were concentrated using Amicon® centrifugal filter devices (MWCO 10 kDa, Millipore, UK) and protein concentrations determined as previously described. EGF and TGF-β1 concentrations were determined using ELISA duo kits (R & D Systems, UK) with microplates pre-coated with monoclonal antibodies specific for the human markers in question, as per manufacturer's instructions. Sample absorbances were read at 450 nm and concentrations were then calculated from a standard curve of known values, and subsequently normalised against protein concentration.

Biochemical Stability of Preserved Amnion

Three AM segments from 3 different donor samples preserved as previously described were stored in sterile vacuum pouches at ambient temperature and away from direct light, for a period of 4, 8, 12, 24, 48 and 60 weeks. Following storage, soluble proteins were extracted from the tissue sections and protein concentrations determined in each sample prior to EGF and TGF-β1 ELISAs.

Immunofluorescence

AM segments from 3 donors for each sample preservation type were prepared and immunostained according to published methodologies. Briefly, AM sections were out-spread, epithelial side up on a flat surface, a layer of optimal cutting temperature (OCT) freezing compound (Leica, Germany) applied to the surface and a piece of microscope tissue slightly larger than the tissue section was placed on top. Using the microscope tissue, the amnion was repeatedly folded (5-7 mm per fold) ensuring any air bubbles between folds were expelled and then 1 cm sections of the folded tissue section were carefully placed vertically into pre-moulded aluminium foil cups (1.5 cm in height) containing pre-chilled OCT compound and immediately frozen using liquid nitrogen. Once frozen the samples were either stored at −80° C. or 6 nm sections were prepared using a cryostat (Leica), blocked and directly stained with primary antibodies, overnight, at 4° C. (Table 1). Primary antibodies were detected using secondary anti-mouse (A11029) and anti-rabbit (A21430, both from Invitrogen, Paisley, UK) fluorophore conjugates applied at 1:400 and incubated for 1 h at room temperature. Slides were counterstained with 4',6-Diamidino-2-phenylindole (DAPI; 1.25 ng/mL; Santa Cruz, Germany). Slides were examined on a fluorescence microscope (Olympus BX51) and imaged using Cell^F software (Olympus, UK). Each experiment was performed in triplicate.

TABLE 1

A summary of primary antibodies used in this study

| Target | Source | Clone | Species Raised | Dilution Factor |
|---|---|---|---|---|
| BDNF | abcam[a] | ab72439 | rabbit | 1:20 |
| EGF | R & D[b] | MAB236 | mouse | 1:20 |
| E-Selectin | abcam | ab6630 | mouse | 1:100 |
| HGF | R & D | AF-294-NA | goat | 1:7 |
| ICAM-1 | abcam | ab20 | mouse | 1:20 |
| IL-8 | abcam | ab89336 | mouse | 1:20 |
| KGF | abcam | ab9598 | rabbit | 1:1000 |
| MMP2 | abcam | ab7032 | mouse | 1:500 |
| MMP3 | abcam | ab18898 | mouse | 1:33 |
| MMP9 | abcam | ab51203 | mouse | 1:250 |
| β-NGF | abcam | ab6199 | rabbit | 1:100 |
| PEDF | abcam | ab14993 | mouse | 1:20 |
| TGF-β1 | R & D | MAB240 | mouse | 1:25 |
| TSP-1 | abcam | ab1823 | mouse | 1:100 |

(Abbreviations: BDNF, brain derived neurotrophic factor; HGF, hepatocyte growth factor; ICAM-1, intercellular adhesion molecule-1; IL-8, interleukin-8; KGF, keratinocyte growth factor; MMP, matrix metalloprotease; NGF, nerve growth factor; PEDF, pigment epithelium derived factor; TGF, transforming growth factor; TSP, thrombospondin.
[a]abcam, UK.
[b]R & D Systems, Oxfordshire, UK.)

Cell Culture

Primary corneal epithelium (pCEC): Cells were isolated according to a previously published methodology [Shanmuganathan, V. A., et al., The British journal of ophthalmology, 2006. 90(1): p. 55-8] and cultured in CnT-BM.1 basal medium containing CnT-20.A, B and C supplements (CellnTec, Switzerland), 2.5 µg/mL Plasmocin (Autogen Bioclear, UK), and 0.02 µg/mL gentamicin, 0.5 ng/mL amphotericin B (combination, Gibco, Invitrogen, UK).

Keratocyte culture: Keratocytes were isolated according to a previously published methodology [Branch, M. J., et al., Invest Ophthalmol Vis Sci, 2012. 53(9): p. 5109-16.] and cultured in basal culture medium M199 (Sigma-Aldrich) filter-sterilized by using a 0.20 µm filter (Minisart High-Flow, Sartorius Stedim Epsom, UK).

Corneal epithelial cell line: hiCEC (immortalised human corneal epithelial cells, passages 19-26; a kind donation from Araki-Sasaki, Japan[Araki-Sasaki, K., et al., Invest Ophthalmol Vis Sci, 1995. 36(3): p. 614-21.]) were expanded in EpiLife culture medium (Invitrogen, UK). All cultures were maintained at 37°C under 5% v/v $CO_2$, replacing culture medium every 2-3 days until confluent. Where necessary cells were passaged using TrypLE™ Express (Invitrogen) and cell counts were carried out using Trypan Blue (Sigma-Aldrich).

In Vitro Culture Model

FrAM and membranes preserved using different methods were cultured directly or indirectly with hiCEC, pCEC and keratocytes. Indirect cultures were constructed using 24-well CellCrown™ inserts (Scaffdex, Finland). 15 mm membrane discs were laid over the support and held in place with an outer ring. The support was then inverted in a 24-well plate so it was immersed in the media but not in direct contact with the cells. Direct cultures were assembled by seeding the cells directly on top of the AM/CellCrown™ supports and not in the cell culture plates. Cells were seeded at 0.05×106 and maintained at 37° C. under 5% v/v $CO_2$ for 3 days and then used in the following assays:

Biochemical release: Factor time release studies were carried out using the above system apart from the membranes were submersed in sterile PBS. Samples of PBS (120 µl) were taken following 1, 2, 4 and 10 days in culture. Samples were stored at −80° C. prior to SearchLight protein array analysis (Aushon Biosystems), and for use in-house EGF and TGF-β1 ELISAs.

Biocompatibility assays: Cell proliferation was assessed using the in vivo Cell-8 assay (Sigma-Aldrich), cytoxicity was measured using a lactate dehydrogenase (LDH) enzyme based assay (Roche Diagnostics Ltd, UK) and apoptosis was determined using a caspase-3 colorimetric assay (R & D Systems, UK). All assays were performed according to manufacturer's protocols.

Cell migration assay: A scratch wound closure assay was performed five days post seeding, on confluent cultures starved of serum and EGF for 24 hours. A standard single linear scratch with a defined length of 1.6 cm was created in the cell monolayers across each well using a 10 µl pipette tip, giving a 300 µm wound width. Unattached cells were washed away and medium was replaced with media containing EGF and foetal calf serum. Wounds were photographed immediately (day 0) and then 2, 4, 6 and 10 days, at four pre-determined positions by phase-contrast imaging at 100× magnification. Wound healing for each culture was reported as the average linear speed of the wound edge closure over a 10 day period using ImageJ software (Wayne Rasband, National Institute of Health).

Statistical Analysis

Results are presented as mean±SEM. Statistical analyses were performed using the nonparametric Mann-Whitney U test and $p<0.05$ was considered significant.

Preclinical Assessment of Vacuum-Dried Amniotic Membrane Omnigen™ in a Pilot Animal Study Epithelial defect healing assessment: The untreated epithelial defects in all treatment groups appeared standardised at around 80% coverage of the ocular surface (Table 6 and FIG. 11 A). Defects appeared to heal in a similar manner in all groups. The rationale for this is that the wound injury created is not severe enough to delay epithelial recovery in untreated samples and that maximum rate of epithelial recovery occurs in the control. Vacuum-dried amniotic membrane prepared according to the present invention without a freezing step before freeze drying (Omnigen™) performed equivalently to conventional cryo-preserved amnion. Future planed pre-clinical investigations will involve greater involvement of limbal damage and therefore stem cell loss to slow natural recovery. It is expected that Omnigen™ will demonstrate greater performance in more severe injury types.

Degree of Redness (Table 6 and FIG. 11 B): Similarly to epithelial defect scoring, it was concluded that the injury induced in the pilot study was not sufficiently severe to elucidate any beneficial effect of the amnion treatment over untreated control. Inflammation (redness) naturally decreases over 24 hours.

TABLE 6

Showing the blind clinical assessment data of clinical images of injured eyes

| Image | Treatment | Size of epithelial defect (% estimate) | | | Degree of redness (grade 1, 2, 3, −3 worst) | | | Corneal clarity (grade 1, 2, 3 with 1 being the best)) | | | Limbal ischaemia (yes/no) | |
|---|---|---|---|---|---|---|---|---|---|---|---|---|
| | | Pre | Post | Difference | Pre | Post | Difference | Pre | Post | Difference | Pre | Post |
| 1 | Control | 85 | 46 | 39 | 2 | 1 | 1 | U | U | N/A | U | U |
| 2 | Control | 86 | 46 | 40 | 2 | 1 | 1 | U | U | N/A | U | U |
| 3 | Control | 91 | 48 | 43 | 2 | 1 | 1 | 3 | 2 | 1 | U | U |
| 4 | Dry | 78 | 47 | 31 | 3 | 1 | 2 | 3 | 2 | 1 | no | no |
| 5 | Dry | 76 | 44 | 32 | 3 | 1 | 2 | 3 | 2 | 1 | no | no |
| 6 | Dry | 75 | 41 | 34 | 3 | 2 | 1 | 3 | 2 | 1 | no | no |
| 7 | Control | 81 | 51 | 30 | 2 | 1 | 1 | 3 | 3 | 0 | no | no |
| 8 | Control | 76 | 55 | 21 | 2 | 1 | 1 | 3 | 3 | 0 | no | no |
| 9 | Control | 75 | 60 | 15 | 3 | 2 | 1 | 3 | 3 | 0 | no | no |
| 10 | Wet | 77 | 46 | 31 | 3 | 1 | 2 | 3 | 2 | 1 | no | no |
| 11 | Wet | 88 | 46 | 42 | 2 | 1 | 1 | 3 | 2 | 1 | no | no |
| 12 | Wet | 88 | 38 | 50 | 2 | 1 | 1 | 3 | 2 | 1 | no | no |

TABLE 6-continued

Showing the blind clinical assessment data of clinical images of injured eyes

| Image | Treatment | Size of epithelial defect (% estimate) | | | Degree of redness (grade 1, 2, 3, –3 worst) | | | Corneal clarity (grade 1, 2, 3 with 1 being the best)) | | | Limbal ischaemia (yes/no) | |
|---|---|---|---|---|---|---|---|---|---|---|---|---|
| | | Pre | Post | Difference | Pre | Post | Difference | Pre | Post | Difference | Pre | Post |
| 13 | Control | 88 | 31 | 57 | 2 | 1 | 1 | 3 | 2 | 1 | no | no |
| 14 | Control | 87 | 43 | 44 | 3 | 1 | 2 | 3 | 3 | 0 | no | no |
| 15 | Control | 91 | 45 | 46 | 3 | 1 | 2 | 3 | 3 | 0 | no | no |
| 16 | Dry | 92 | 67 | 25 | 2 | 1 | 1 | 3 | 3 | 0 | no | no |
| 17 | Dry | 91 | 47 | 44 | 2 | 1 | 1 | 3 | 3 | 0 | no | no |
| 18 | Dry | 95 | 50 | 45 | 2 | 1 | 1 | 3 | 3 | 0 | no | no |

Corneal Clarity (Table 6 and FIG. 11 C): Omnigen™ appeared to improve corneal clarity over 48 hours compared to CPAM. With an increased injury severity and greater experiment numbers, these findings will be solidified.

This data confirms conventional clinical assessment are generally highly subjective crude methods for assessing injuries and are therefore not effective methods for detecting subtle differences between treatments. Inducing a more severe epithelial injury will lead to greater data representation.

TEM analysis of untreated central corneal wounds 48 (n=2) hours after injury clearly showed, compared to unburned corneas, extensive stromal damage and disorganisation with considerable stromal cell loss (FIG. 12, A). It was evident that the initial damage continues to degrade over the 48 hours, which is the classical 'acute phase' injury. Putting this into context, this is the period during which many injured soldiers also do not receive effective treatment following battlefield injuries. On the other hand unexpectedly large numbers of stromal cells were seen in the out wound area (FIG. 12 C), indicating massive proliferative activity which most likely leads to undesirable scar forming cascade. While epithelial cells were seen on the corneal surface, these are not representing normal corneal epithelial multi-layered architecture. Overall untreated corneas although appearing to progressively heal in the clinical observations, appear to be an extremely unhealthy condition at the cellular level which will undoubtedly lead to long term visual disturbances.

Treatment with Omnigen™ (n=2) had clear benefits. A recovering multi-layered healthy epithelium could be seen in the central wound region with greatly reduced damage to the cornea stroma (FIG. 12B). Surviving corneal stromal cells were still detected, most likely limiting the stromal degradation seen in FIG. 12A. When the outer wound areas were assessed, a fully stratified and healthy epithelial sheet appears to have been restored, and what appears to be normal stroma containing normal stromal cell distributions. Overall, the pilot data suggested Omnigen™ provides a marked improvement in wound recovery compared to untreated. Due to its dry and transportable nature Omnigen™ is the only treatment that it is possible to use on injured soldiers during the acute (48 hours) window because other preserved amniotic membranes, such as frozen membranes, cannot be stored in conditions close to the battlefield.

1. Gene Analysis

Purpose:

Molecular analysis of cellular activity during different states on injury may provide a greater insight into wound healing and aid to discern the subtle changes induced by different treatments. Genes implicated in human corneal wound healing were selected as targets to assess the activity of wound healing in chemically injured rabbit corneas receiving no treatment or following treatment with cryopreserved amniotic membrane (CPAM) or Omnigen™. PCR probes for rabbit specific genes were then obtained and RT-PCR analysis was performed on RNA extracted from samples obtained from the pilot study.

Outcome: Due to this analysis being carried out on pilot study animals, for each condition a single biological replicate (N=1) was obtained but analysed in triplicate (N=3). Normalised gene expression levels for each gene of interest in central cornea and wound edge (where stem cell activity is most likely) were assessed at 8, 24 and 48 hours and the data represented in FIG. 13.

Epidermal growth factor (EGF) is the major protein involved in epithelial regeneration. Increased expression in cells would suggest increased wound healing activity in this area. In untreated chemically injured rabbit corneas, the expression of EGF was similar between central and peripheral cornea and this expression only slightly increases at the 48 hour time point in the outer wound area (FIG. 13 A-C). However, following treatment with CPAM or Omnigen™, EGF expression notably increased at 8 hours in the peripheral corneal region, which continued to increase up to as much as 4× increase at 48 hours. Interestingly, an EGF expression level was higher with Omnigen™ treatment than with CPAM at all time points. This is evidence that AM promotes wound healing at the outer edge of the wound where it is expected epithelial regeneration originates. More importantly, Omnigen™ is superior at promoting this healing activity.

Transforming growth factor 1 (TGFβ1) has been implicated as a further indicator of corneal wound healing. Again higher gene expression levels would indicate greater wound healing activity. Expression of TGFβ1 in rabbit corneal in untreated chemically injured corneas appeared to marginally increase in central cornea from around 1.5 fold to 2 fold over 48 hours, but expression in outer wound area doubled at hours (4 fold) which then appeared to decrease at 48 hours. Amnion treatment with CPAM and Omnigen™ followed a similar pattern but at slightly more pronounced expression levels in outer wound region suggesting greater wound healing activity. Omnigen™ appeared to promote greater TGFβ1 expression levels than CPAM at all time points, up to as much as 6 fold expression in out wound areas at 24 hours. This is further molecular evidence that Omnigen™ may have greater wound healing potential than CPAM.

Collagen IV is a basement membrane protein essential for epithelial, particular progenitor cell, attachment and recovery. Increased collagen IV gene expression would indicate more effective epithelial recovery in terms of cellular migration and stromal remodelling, and therefore more enhanced wound healing. In untreated chemically injured rabbit corneas, collagen IV expression remained relatively unchanged in central cornea wound areas. This is to be expected as no epithelial cells were present in the central region unto around 48 hours. At the 24 and 48 time points, a slight increase in gene expression was noted (>2 fold greater) in the outer wound region suggesting moderate increase in wound healing and natural epithelial recovery. However, following treatment with amnion, particular Omnigen™ there was a market increase in collagen IV gene expression in central and more so outer wound regions. Omnigen™ appeared to induce ~50% greater gene expression compared to CPAM, which suggests Omnigen™ promotes more effective corneal epithelial regeneration. MMP 9 is the metalloprotease expressed by cells associated with matrix remodelling and specifically in the remodelling of the basement membrane by expanding limbal epithelium during corneal regeneration. The expression profiles for MMP-9 were similar to that of Collagen IV further supporting improved wound healing by amniotic membrane but more specifically Omnigen™ over CPAM.

Hepatocyte growth factor (HGF) regulates cell growth and cell motility and has been implicated as a major factor involved in tissue regeneration secreted by mesenchymal stem cells. There was no obvious trend in expression of HGF in our samples, most likely due to low sample number and possibly due to applying human rationale to an animal model.

This preliminary molecular investigation clearly suggests that amniotic membrane improves wound healing and cellular regeneration when applied during the essential acute stage of injury. More importantly this is evidence that Omnigen™ has superior properties over conventional cyropreserved membrane in vivo confirming our previous in vitro data. Further analysis in a larger sample number is required to statistically validate this preliminary data, but it also demonstrates a clear disparity to clinical observations and more specific modes of quantitative assessment. Although epithelial recover and defect closure appears to be the same across all groups, increased regeneration is clear following treatment with Omnigen™. Omnigen™ may therefore provide greater benefit for a more effective long term recovery of more severe corneal injuries and may therefore explain the marginal in corneal clarity in the clinical observations.

Bio Burden Testing

Purpose: When developing products derived from biological tissues, bioburden testing is an essential component of manufacturing development. This project has employed bioburden testing in three aspects of Omnigen™ development (illustrated in FIG. 14); A) Testing the intrinsic bioburden of fresh amniotic membrane; B), validating antibiotic washes as a primary sterilisation step; C) Validate drying as a secondary sterilisation step; and D) optimisation of terminal sterilisation to minimise the gamma irradiation dose (see terminal sterilisation section).

Even under aseptic conditions, microbial contamination of amniotic membrane is likely. This contamination may originate from the tissue per se, the environment and the personal involved in the delivery, or during procurement, processing, handling and packaging of the tissue. Therefore using non-sterile amniotic membrane is associated with a high risk of infectious disease transmission.

Previous studies show that the bioburden of fresh amnion (when assessing 159 samples) is reported to be around 1×105/100 cm2. Processing amnion for clinical use can reduce this bioburden, prior to sterilization, to a level ranging between from 100 (n=5) to 103/100 cm. In total 39% of the 159 AM tested had a bioburden of 101-102/100 cm and 55% in the range of 102-103/100 cm. The bioburden of lyophilised amnion (15×12 cm) can be on average about 572 cfu (SD 209)(102-103/100 cm). This is comparable to that of fresh processed amnion. This suggests the lyophilisation process does not contribute to bioburden reduction. A summary of known bioburden microbes are summarised in Table 7.

It is important to note here that membranes obtained in previous bioburden studies were obtained from normal vaginal delivery (NVD) and not elective caesarian sections (ESC). Reported contaminating microbes of the amniotic membrane are detailed below, and normally originate from the vaginal microbial flora. Therefore, the bioburden would be expected to be lower in membranes obtained via elective caesarian sections as they haven't passed through the vaginal area.

Previous studies compared the bioburden (pre-processing bacterial load) of vaginal delivery and ESC and found 22 different species. They found that NVD had up to 4 species contamination whilst ESC had 3. 40% of NVD were vaginal and gut organisms compared to 10% of elective caesarian sections. In both, skin organisms were the most common. It is proposed that the ESC contamination is through handling in the theatre, and that an immediate aggressive decontamination step might eliminate the majority of contamination here.

TABLE 7

Literature based reports of amniotic membrane bioburden

| Bug | Normal Vaginal delivery (NVD) | ESC |
|---|---|---|
| Bacillus sp | | (1)[52] |
| Bacteroides fragilis | (1)[52] | |
| Bacteroides vulgatus | (1)[52] | |
| Bifidobacterium adolescentis | (1)[52] | |
| Bifidobacterium sp | (1)[52] | |
| Diphtheroid (skin) | (6)[52] | (4)[52] |
| Enterococcus faecalis | (2)[52] | (1)[52] |
| Escherichia coli | (2)[52] | |
| Lactobacillus sp | (1)[52] | |
| Micococcus kristinae | | (1)[52] |
| Propionibacterium acnes ((skin)) | (3)[52] | (8)[52] |
| Propionibacterium avidum | | (1)[52] |
| Shigella sp | (1)[52] | |
| Staph aureus | (1)[52] | |
| Staph epidermidis (skin) | (5)[52] | (5)[52] |
| Staph haemolyticus | (1)[52] | (1)[52] |
| Staph intermidis | (1)[52] | (1)[52] |
| Staph lugdunenis | (1)[52] | (1)[52] |
| Strep agalactiae | (1)[52] | |
| Strep constellatus | (1)[52] | |
| Strep gordonii | | (1)[52] |
| Strep vestibularis | (1)[52] | |
| Pseudomonas aeruginosa | [53] | N/A |
| Pseudomonas capacia | [53] | N/A |
| Pseudomonas maltophilia | [53] | N/A |
| Entreobacter agglomerans | [53] | N/A |
| Serratia plymtica | [53] | N/A |
| Staphepidermis | [53] | N/A |

It is reported that the incidence of microbial infection following amniotic membrane transplantation is 3.4% (although the storage media were culture negative). This was reduced to 1.6% when prepared in commercial, good manufacturing practice (GMP) laboratories. Of the infections that occurred only 5% occurred within the first month after amniotic membrane transplantation and these did not correlate to the underlying clinical diagnosis suggesting they may not be directly related to contaminated amnion. Use of non-preserved amniotic membrane however is faced with serious threat of infection. Amnion has been shown to be effective in adhering microbial contaminants, such as *Staphylococcus epidermidis*, indicating it is essential to prepare membranes in a microbe-free environment.

TABLE 8

Bioburden of assessment of freshly elective caesarean section obtained amniotic membrane
A Bacterial Identification

| AM Sample | i) Aerobic (48 hours) | ii) Anaerobic (7 days) | iii) Aerobic (48 hours) from ii | iv) Colony in broth (7 Days) |
|---|---|---|---|---|
| 1 | *Neisseria cinerea* | NG | NG | NG |
| 2 | *Micrococcus* sp | 100 cfu/mL | *Micrococcus* sp | *P. acnes* |
| 3 | NG | 30 cfu/mL | NG | *Micrococcus* sp *P. acnes* *Staph schleiferi* |
| 4 | NG | NG | NG | NG |
| 5 | NG | NG | *Micrococcus* sp | NG |
| 6 | NG | NG | NG | *Micrococcus* sp |
| 7 | NG | NG | *Micrococcus* sp | NG |
| 8 | NG | NG | NG | NG |
| 9 | NG | NG | NG | NG |
| 10 | NG | NG | NG | NG |

Therefore, if prepared in an appropriate GMP environment risk of infection from amnion is low or even eliminated.

Outcome:

Working with the Biomaterials Related Infection Group encountered regulatory problems. Bioburden experiments required us to submit a substantial amendment to the Nottingham Research Ethics Committee (NREC) incorporating the methodology into our original application.

Bioburden of Fresh Amniotic Membrane—Before Washing (Normal Flora):

Assessing the natural floral contamination of 10 fresh amniotic membranes revealed that bioburden of membranes obtained from the QMC via elective caesarian sections was expectably lower than literature reported of normal vaginal devilries. 40% of our amnion tested showed no signs of bioburden contamination (Table 8). Of those that demonstrated contamination, *Neisseria cinerea*, and *Micrococcus* sp were the most common source of contamination, most likely from skin. This indicates the risk of major contamination is low from manufacturing Omnigen™ using membranes obtained through elective caesarian sections.

Validate Antibiotics as a Sterilisation Step—Post Washing with Antibiotics:

10 fresh amniotic membrane were subjected to the standard manufacturing process including an antibiotic washing step (Table 9). Before the drying phase, samples were taken and subjected to bioburden testing revealing that all samples were negative for microbial growth. This indicated the antibiotic treatment is sufficiently effective to be considered a sterilisation step.

TABLE 9

Bioburden of assessment of freshly elective caesarean section obtained amniotic membrane processed in the presence of an antibiotics wash
B Bacterial Identification

| AM Sample | i) Aerobic (48 hours) | ii) Anaerobic (7 days) | iii) Aerobic (48 hours) from ii | iv) Colony in broth (7 days) |
|---|---|---|---|---|
| 1 | NG | NG | NG | NG |
| 2 | NG | NG | NG | NG |
| 3 | NG | NG | NG | NG |
| 4 | NG | NG | NG | NG |
| 5 | NG | NG | NG | NG |
| 6 | NG | NG | NG | NG |
| 7 | NG | NG | NG | NG |
| 8 | NG | NG | NG | NG |
| 9 | NG | NG | NG | NG |
| 10 | NG | NG | NG | NG |

C. Validate Drying as a Sterilisation Step (No Antibiotic Wash) Drying:

Similarly, bioburden testing of the dry phase alone, without any antibiotics was, also indicated a high efficiency of eliminating any contaminating microbial flora, with only one sample from 10 membranes testing positive (Table 10). Therefore, combined antibiotics and drying will ensure complete elimination of bioburden from natural microbial flora, most likely even if high levels of contamination were expectedly observed.

TABLE 10

Bioburden of assessment of amniotic membrane processed in an antibiotic free system and then dried.
C Bacterial Identification

| AM Sample | i) Aerobic (48 hours) | ii) Anaerobic (7 days) | iii) Aerobic (48 hours) from ii | iv) Colony in broth (7 days) |
|---|---|---|---|---|
| 1 | NG | NG | NG | NG |
| 2 | NG | NG | NG | NG |
| 3 | NG | NG | NG | NG |
| 4 | NG | NG | NG | NG |
| 5 | NG | NG | NG | NG |
| 6 | NG | NG | *Micrococcus* sp | NG |
| 7 | NG | NG | NG | NG |
| 8 | NG | NG | NG | NG |
| 9 | NG | NG | NG | NG |
| 10 | NG | NG | NG | NG |

A sterility assurance level (SAL) of $10^{-6}$ is the set requirement for medical items intended for contact with human tissue. Each SAL describes themicrobial population that was destroyed during sterilisation i.e. each log reduction ($10^{-1}$) represents a 90% reduction in microbial populations. Therefore a 6-log reduction will reduce a population of million organisms ($10^6$) to practically zero. It is common to employ overkill cycles to provide greatest assurance of sterility for critical products such as implantable devices. Therefore, membrane segments have been artificially loaded with *Neisseria cinerea*, and *Micrococcus* sp at a concentration greater than $10^{-6}$ to demonstrate a SAL for each step of Omnigen™ manufacture.

2. Antibiotic Properties

Purpose:

Amniotic membrane is reported to possess anti-microbial properties, which may be beneficial in preventing and controlling infection as a battlefield application. Elucidating and validating the ability of amnion to mediate infection may eliminate the need for additional topical application of antibiotics, essentially creating a single treatment.

Outcome:

Cryo-preserved amniotic membrane prepared without the presence of antibiotics in the pre-preservation manufacturing procedure possessed extremely poor (if any clinically significant) antimicrobial properties (Table 11 and Table 12). Any microbicidal property is variable and faint between membranes. Following further investigation, it was discovered that membranes prepared in the presences of antibiotics and then extensively washed, even after preservation, retained residual microbicidal potency of antibiotics (Table 13 and Table 14). An explanation of this is that amnion acts as a reservoir for antibiotics, which are sequestered into and remain in the stromal matrix of the material, even after preservation and washing. Considering these findings, our evidence suggests that literature based reports indicating antimicrobial properties in fact used membranes prepared and stored in antibiotic containing solutions. Despite washing following cryo-preservation, sequestered antibiotic are appear to be responsible for the reported property.

Innovation:

Exploiting this reservoir property of amniotic membrane and combining this with drying process of Omnigen may provide powerful and lasting anti-infective property in a clinical situation. Therefore the amniotic membrane may be infused with a cocktail (Gentamicin 200 mg/ml, Imipenem 10 mg/nnl, Nystatin 125,000 U/ml, Polymyxin B 10 mg/ml, Vancomycin 2.5 mg/ml) of antibiotics at 'clinical efficacy' concentration, immediately prior to the drying process. This means that upon in vivo reconstitution, Omnigen™ will release a burst of soluble antibiotics following by a prolonged and sustained protective effect. Essentially Omnigen™ could be a single treatment to facilitate and improve wound healing whilst providing lasting protection against infection.

TABLE 11

Minimum Inhibitory Concentration (MIC) of AM extracts without antibiotic treatment against a panel of gram negative and gram positive bacteria.

| | | S. aureus $10^6$ CFU/mL MIC | | | | S. epidermidis $10^6$ CFU/mL MIC | | | |
|---|---|---|---|---|---|---|---|---|---|
| Wells | % | AM234 | AM235 | AM236 | Gent | AM234 | AM235 | AM236 | Gent |
| 1 | 100 | + | + | − | − | − | + | + | − |
| 2 | 50 | + | + | − | − | + | + | + | − |
| 3 | 25 | + | + | + | − | + | + | + | − |
| 4 | 12.5 | + | + | + | − | + | + | + | − |
| 5 | 6.25 | + | + | + | − | + | + | + | − |
| 6 | 3.13 | + | + | + | − | + | + | + | − |
| 7 | 1.56 | + | + | + | − | + | + | + | − |
| 8 | 0.78 | + | + | + | + | + | + | + | + |
| 9 | 0.39 | + | + | + | + | + | + | + | + |
| 10 | 0.20 | + | + | + | + | + | + | + | + |
| 11 | 0.10 | + | + | + | + | + | + | + | + |
| 12 | − | − | − | − | − | − | − | − | − |

| | | Diptheroid $10^6$ CFU/mL MIC | | | | Moraxella $10^6$ CFU/mL MIC | | | |
|---|---|---|---|---|---|---|---|---|---|
| Wells | % | AM234 | AM235 | AM236 | Gent | AM234 | AM235 | AM236 | Gent |
| 1 | 100 | + | + | + | − | + | + | − | − |
| 2 | 50 | + | + | + | − | + | + | + | − |
| 3 | 25 | + | + | + | − | + | + | + | − |
| 4 | 12.5 | + | + | + | − | + | + | + | − |
| 5 | 6.25 | + | + | + | − | + | + | + | − |
| 6 | 3.13 | + | + | + | − | + | + | + | − |
| 7 | 1.56 | + | + | + | − | + | + | + | + |
| 8 | 0.78 | + | + | + | − | + | + | + | + |
| 9 | 0.39 | + | + | + | + | + | + | + | + |
| 10 | 0.20 | + | + | + | + | + | + | + | + |
| 11 | 0.10 | + | + | + | + | + | + | + | + |
| 12 | − | − | − | − | − | − | − | − | − |

(+) showed growth of microorganism, (−) no growth of microorganisms, well 11 positive control, well 12 negative control. The results are average values triplicate experiments.

TABLE 12

MIC and MBC (Minimum Bactericidal Concentration) of AM extracts without antibiotic treatment against a panel of gram negative and gram positive bacteria.

| Bacterial Strain | AM234 | | AM235 | | AM236 | |
|---|---|---|---|---|---|---|
| | MIC (%) | MBC (%) | MIC (%) | MBC (%) | MIC (%) | MBC (%) |
| S. aureus | 100 | 100 | 100 | 100 | 25 | 25 |
| S. epidermidis | 50 | 100 | 100 | 100 | 100 | 100 |
| Diptheroid | 100 | 100 | 100 | 100 | 100 | 100 |
| Moraxella | 100 | 100 | 100 | 100 | 50 | 100 |

TABLE 13

Minimum Inhibitory Concentration (MIC) of AM extracts following antibiotic treatment against a panel of gram negative and gram positive bacteria.

| Wells | % | AM234 | AM235 | AM236 | Gent | AM234 | AM235 | AM236 | Gent |
|---|---|---|---|---|---|---|---|---|---|
| 1 | 100 | − | − | − | − | − | − | − | − |
| 2 | 50 | − | − | − | − | − | − | − | − |
| 3 | 25 | − | − | − | − | − | − | − | − |
| 4 | 12.5 | − | − | − | − | − | − | − | − |
| 5 | 6.25 | + | − | + | − | + | − | + | − |
| 6 | 3.13 | + | + | + | − | + | − | + | − |
| 7 | 1.56 | + | + | + | − | + | − | + | − |
| 8 | 0.78 | + | + | + | + | + | + | + | + |
| 9 | 0.39 | + | + | + | + | + | + | + | + |
| 10 | 0.20 | + | + | + | + | + | + | + | + |
| 11 | 0.10 | + | + | + | + | + | + | + | + |
| 12 | − | − | − | − | − | − | − | − | − |

| Wells | % | AM234 | AM235 | AM236 | Gent | AM234 | AM235 | AM236 | Gent |
|---|---|---|---|---|---|---|---|---|---|
| 1 | 100 | − | − | − | − | − | − | − | − |
| 2 | 50 | − | − | − | − | − | − | − | − |
| 3 | 25 | − | − | − | − | − | − | − | − |
| 4 | 12.5 | + | + | − | − | − | − | + | − |
| 5 | 6.25 | + | + | − | − | − | + | + | − |
| 6 | 3.13 | + | + | + | − | + | + | + | − |
| 7 | 1.56 | + | + | + | − | + | + | + | + |
| 8 | 0.78 | + | + | + | − | + | + | + | + |
| 9 | 0.39 | + | + | + | + | + | + | + | + |
| 10 | 0.20 | + | + | + | + | + | + | + | + |
| 11 | 0.10 | + | + | + | + | + | + | + | + |
| 12 | − | − | − | − | − | − | − | − | − |

(+) showed growth of microorganism, (−) no growth of microorganisms, well 11 positive control, well 12 negative control. The results are average values triplicate experiments

TABLE 14

MIC and MBC (Minimum Bactericidal Concentration) of AM extracts following antibiotic treatment against a panel of gram negative and gram positive bacteria. The results in all tables are shown as average values from three separate experiments.

| Bacterial Strain | AM234 MIC (%) | AM234 MBC (%) | AM235 MIC (%) | AM235 MBC (%) | AM236 MIC (%) | AM236 MBC (%) |
|---|---|---|---|---|---|---|
| S. aureus | 6.25 | 6.25 | 3.13 | 6.25 | 6.25 | 12.5 |
| S. epidermidis | 6.25 | 12.5 | 0.78 | 3.13 | 6.25 | 12.5 |
| Diptheroid | 12.5 | 12.5 | 12.5 | 12.5 | 3.13 | 6.25 |
| Moraxella | 3.13 | 6.25 | 6.25 | 6.25 | 12.5 | 25 |

Packaging
Purpose:

Omnigen™ may be created and marketed as a fully and easily transportable off the shelf product that is easily utilisable in any situation. Packaging is therefore an important aspect of an effective product, requiring specific considerations such as providing appropriate product protection, long term preservation and then application mode as well as ease of application. The packaging prototype has therefore been generated.

Outcome:

We have worked closely with Steripack and Phase 3 plastics to conceptualise and devise the most appropriate packaging for Omnigen™. The immediate key considerations/requirements for Omnigen™ packaging were:

Protecting the Omnigen™ disks during storage and transport: A rigid package of some kind is preferable to support the Omnigen™ disks.

Combining protection/rigidity with an innovative delivery system would be a way forward. Delivering Omnigen™ in tray to hold the disc; offers protection from transit damage; offers ease of handing in and out of the pouch; a tray would also offer application assistance where the product requires re-hydration.

Packaging needs to consider application requirements. Omnigen™ may be used in a sterile surgical environment therefore and therefore may have dual (inner and outer) packaging akin to most surgical materials. However, for use in an emergency non-medical environment, packaging may be easily accessible for direct access to the product.

Stability over long term (>5 years) and in a range of environmental conditions is an advantage for Omnigen™ packaging. The product packaging is advantageously vacuum-sealed and sterilized for a long shelf life—as well as being validated from a regulatory point of view for the proposed shelf life. Due to the possibility of military and civilian application in an outside environment, exposure to light damage is also possibility and requires consideration.

Based the above requirements/considerations, prototype packaging has been designed for application testing.

Delivery tray: Handling Omnigen as little as possible would prevent product being compromised. Therefore Phase 3 plastics designed a tear-drop shaped tray made from gamma stable PETG film to hold the Omnigen™ disks (FIG. 15). This offers protection for Omnigen™ during transit as the vacuum package will hold the disk in place, but the tear-drop handle will facilitate ease of handling both in and out of the packaging.

Packaging: Working with Steripack in conjunction with Phase 3 plastics, packaging designed for Omnigen™ was a dual pouch system. The inner pouch, seen above is a heat sealable foil pouch, which can withstand a vacuum being pulled on sealing. The vacuum will act as a restriction to movement of the disc in the tray. The concept is that the pouch is peel able in format and the grey flap (FIG. 16) is pulled to expose the tear drop tray handle, which can then be slid out of the pouch. The inner pouch (with label—FIG. 17) will then be inserted into an outer Tyvek/Film pouch (with label—FIG. 17), which is also peelable (FIG. 16). The entire packaging once sealed will be terminally sterilized to create a system application for theatre of emergency situations.

Acetated Age Testing—Shelf Life Validation

Purpose: An important aspect or validating Omnigen™ for military application as well as an effective commercial product will be demonstrating a long shelf-life for Omnigen™, typically 3 to 5 years.

Outcome: Due to its dry and stable nature, we anticipate that Omnigen™ can have a shelf life of up to 5 years. Omnigen™ packaging has been designed to allow gamma or e-beam compatibility. Steripack are certified for regulatory approved shelf life testing and will be manufactures at the HTA regulated standards. We have already conducted preliminary investigations comparing the stability of key markers, EGF and TGFb1, over long-term storage in different preparations of amniotic membrane. We compared the stability of cryo-preserved amnion, conventional freeze-dried amnion, trehalose treated and rafinose treated Omnigen™ for 60 weeks. Fresh amnion was used as control. The results revealed cryopreserved amniotic membrane was unstable over 60 weeks progressively decreasing the detectable levels of the markers, particularly TBGFb1. EGF and TGFb1 stability remained constant in Omnigen™ prepared using both trehalose and rafinose over 60 weeks (1 year).

Omnigen

Omnigen is the name given to a freeze dried amniotic membrane. The method of preparation of Omnigen is explained below.

Omnigen TE

Omnigen is a denuded freeze dried amniotic membrane. The method of preparation is the same as for Omnigen below except for a denuding step carried out within the initial processing and preservation stage on fresh amniotic membrane.

The major difference therefore between previous published methodologies and OmnigenTE manufacture is that OmnigenTE is denuded FRESH and not post preservation. This is a surprising progression step for several reasons. Conventionally, AM is not used fresh and must be preserved for a quarantine period before used therefore denuding fresh is unnecessary. IN addition, AM is not available to the end user until post preservation therefore denuding fresh is not an option.

Primarily, for OmnigenTE, denuding is carried out within the initial processing and preservation stage. The rationale for this is that AM is then dry preserved with the intention of being used directly for tissue engineering. Denuding post preservation would require reconstitution of the tissue before denuding which would have to be carried out by the end user and would require expertise, most likely resulting in non-standardised product. OmnigenTE therefore offers a standardised, convenient and easy to use option.

This integrated process and removal of viable epithelium is not found in other amniotic membrane denuding techniques. In the OmnigenTE processing (with a view to commercial production) the amniotic membrane may be treated as a whole rather than cut into portions before treating. The Omnigen TE processing method has been optimised with respect to thermolysin incubation time and number of washes. Finally instead of being shaken manually the AM was placed in a flask and rocked which (again with a view to commercial production) may improve consistency and makes processing easier.

OmnigenTE Denuding Optimisation

AM denuding was optimised using the following variables; time point (9 12, 15 and 20 mins) and temperature (RT and 37° C.). Complete denuding was achieved from 12 mins, at RT (FIG. 19c) when placed on a rocker. While thermolysin also removed AM epithelium from 12 mins 37° C. (FIG. 19d) it was decided that the former methodology (at RT) would be used as it was likely less vigorous and therefore less damaging to the rest of the AM.

An advantage of the procedure is that fresh AM may be treated in a standardised way, prior to preservation, so that the end product is a standardised, convenient and easy to use, 'dry off the shelf' tissue engineering product that simply needs to be opened, reconstituted and used. There is no additional expertise, reagents or materials required by the end user.

Omnigen and Omnigen TE Manufacture Method

Pre-Preparation

Approximately 18 hours before starting the procedure: transfer 1 vial of the antibiotics/antifungal concentrate from the −80° C. freezer to the fridge (2° C.-8° C.) so that it can thaw overnight.

Preparation

After consent, prior to AM arrival—for each additional amniotic membrane another set of materials must be set up.

Collect the following materials and place on to the molecular laboratory bench or trolley:

7×T175 flasks
1×1 L NaCl solution
1×DPBS solution
1×5 ml antibiotics/antifungal concentrate
1× metal forceps
1×10 ml syringe
1×50 ml syringe
1×19G needle
1× marker pen
1× sharps bin
1× square dish pack (sterile)
5× plastic forceps
2× surgical scissors
1× size 22 blade (sterile, individually packaged) and custom holder (sterile, autoclaved)
1× sponge spears (pack)
1× Scalpel Turn on Class II safety cabinet. Sterilise using 2% distel and 70% IMS. Layer blue roll across work surface.

Weigh out 14.86 g of raffinose powder.

Transfer the following materials to the cabinet. Note: clean all materials and packaging with 70% IMS prior to placing them in the cabinet, remove packaging inside the cabinet:

1×T175 flask
1×500 ml DPBS solution
14.86 g raffinose powder
1× marker pen

Mark the 250 ml line on the T175 with a marker pen (to stand out). Open the flask (rest the caps upwards on the cabinet surface) and add raffinose powder. Clearly label 'Pre-filter raffinose'. Add the DPBS to the flask to the 250 ml line. Place the flask on the rocker for 30 mins for raffinose to dissolve.

Label the DPBS bottle (with remaining PBS in) with initials and date and put in cold room for use next time (or for use in the denuding step in Omnigen TE procedure).

Transfer the following materials to the cabinet. Note: clean all materials and packaging with 70% IMS prior to placing them in the cabinet, remove packaging inside the cabinet:
4×T175 flasks
1×IL NaCl solution Using the marker pen, label flasks 'Collection' 'WASH 1', 'WASH 2' and 'WASH 3'. Fill the flasks with 250 ml NaCl solution (rest the caps upwards on the cabinet surface). Close the flasks and set them aside, as they are ready to be used. Discard the empty NaCl solution bottle.

Place the collection flask into a polystyrene box along with a pair of individually sealed, sterile scissors and forceps, 1 pair of blue and one pair of orange gloves and a biohazard bag. This box will be taken when the foetal membrane is collected.

[For Omnigen TE do the Following Additional Steps:
Transfer the following materials to the cabinet. Note: clean all materials and packaging with 70% IMS prior to placing them in the cabinet, remove packaging inside the cabinet:
25 mg Thermolysin
4×T175 flasks
3×DPBS bottle (including previously opened bottle)
Using the marker pen, label flasks 'Thermolysin' and 'TW 1', 'TW 2' and 'TW-3' (wash flasks). Add the thermolysin to the 'Thermolysin' flask.
Mark the 200 ml line on the T175s with a marker pen. Fill the flasks with 200 ml DPBS solution (rest the caps upwards on the cabinet surface). Close the flasks and set them aside, until they are ready to be used.
Discard the empty DPBS bottles. Label the DPBS bottle (with remaining DPBS in) with initials and date and put in cold room for use next time.]

When 30 mins has elapsed since the pre-filtered raffinose was placed on the rocker, check that it has thoroughly dissolved (clear solution, no grains visible on side of flask). Transfer the following materials to the cabinet. Note: clean all materials and packaging with 70% IMS prior to placing them in the cabinet, remove packaging inside the cabinet:
2× Unopened T175 flasks
1×T175 flask labelled 'Pre-filter raffinose'
1×5 ml antibiotics/antifungal concentrate
1× metal forceps
1×10 ml syringe
1×50 ml syringe
2×0.2 μm filter
1×19G needle Clearly label a new T175 flask 'Post-filter raffinose'. Open the flask (rest the caps upwards on the cabinet surface) and using the 50 ml syringe and 0.2 μm filter, filter the raffinose solution into the 'Post-filter raffinose' flask. Change filters if necessary. Replace the cap and remove and dispose of the empty 'Pre-filter raffinose' flask.

Use the metal forceps to remove the metal cap from the antibiotics/antifungal concentrate. Discard the metal cap and the forceps in the sharps bin.

Open the 'Post-filter raffinose' flask (rest the caps upwards on the cabinet surface). Using a 10 ml syringe and 19G needle, withdraw 5 ml antibiotic concentrate from the vial and add it to the flask. Discard the 10 ml syringe, 19G needle and antibiotic vial in the sharps bin. Replace the flask cap.

Swirl the flask thoroughly (6-10 times) to mix.

Open the 'Post-filter raffinose' flask (rest the caps upwards on the cabinet surface). Using the serological pipette and pipette aid, remove 25 ml of the solution and add it to a new T175. Label the flask '10% wash' and using the marker pen, mark the 250 ml line. Fill up to this line (250 ml total volume) with PBS.

Ensure that all flasks are tightly closed; then place towards the back of the cabinet in order ('WASH 1', 'WASH 2', 'WASH 3', 'Post-filter raffinose' and '10% wash')

Remove from the cabinet and discard any materials that are no longer needed:

Transfer the following materials to the cabinet. Note: clean all materials and packaging with 70% IMS prior to placing them in the cabinet, remove packaging inside the cabinet:
1× square dish pack (sterile)
2× plastic forceps
1× surgical scissors
1× size 22 blade (sterile, individually packaged) and custom holder (sterile, autoclaved)
1× screw driver Open the square dish pack and place 2 dishes side by side. The left hand side (LHS) tray will be used for membrane processing whilst the RHS tray will be used for keeping opened sterile instruments. Assemble the blade holder and place on the RHS tray.

Amniotic Membrane Collection

Once AM has been consented and the midwife has rang, take the collection box to the delivery suite, the AM will be in the delivery suite.

Put on both sets of gloves and open the 'Collection' flask (rest the caps upwards on the sink surface).

Using the scissors cut the fetal membrane sac (Amnion and chorion) from the placenta and, using the forceps, place the AM carefully into the flask and replace the cap.

Place the flask in the biohazard bag, and place the bag into the box. Remove gloves and along with the plastic forceps place in orange bin bag in the sluice room. Return surgical scissors to the laboratory for disposal. Transfer the flask to the class II safety cabinet in the molecular laboratory.

Chorion Removal and Amniotic Membrane Washing

Swirl the 'Collection' flask several times until the foetal membrane sac is suspended, placing the flask over the LHS tray, remove the AM using the plastic forceps. Spread the AM out as much as possible using the plastic forceps.

Searching along the edges of the foetal membrane sac there will be an obvious area where the AM and chorion have separated. Placing the sac AM side down, use the plastic forceps to gently peel the chorion away from the AM. Always keep the AM flat against the tray.

Once the AM has been separated from the chorion, using the plastic forceps, place the isolate AM in 'Wash 1' flask. Wipe off any contaminating liquids using blue roll and 70% IMS, ensuring that you can still read the label. Remove from the cabinet and place on the rocker for 20 mins (a timer should be used).

Return the chorion back to the 'Collection' flask. Remove from the cabinet and discard any materials that are no longer needed:
1×'COLLECTION' flask containing the chorion (to which 20% distel should be added to make the total concentration of distel in the flask ≥2%)
1×LHS square dish
2× plastic forceps Replace the following:
1×LHS square dish
2× plastic forceps When the first wash is complete, remove the flask from the rocker and place it to the left of the LHS tray, place 'Wash 2' flask on the right of the LHS tray. Open both flasks (rest the caps upwards on the cabinet surface), transfer the AM from flask 'Wash 1' to 'Wash 2'.

Wipe off any contaminating liquids using blue roll and IMS, ensuring that you can still read the label. Remove from the cabinet and place on the rocker for 20 mins (a timer should be used).

Remove from the cabinet and discard any materials that are no longer needed:

1×'Wash 1' flask (to which 20% distel should be added to make the total concentration of distel in the flask ≥2%).

When the second wash is complete, remove the flask from the rocker and place it to the left of the LHS tray, place 'Wash 3' flask on the right of the LHS tray. Open both flasks (rest the caps upwards on the cabinet surface), transfer the AM from flask 'Wash 2' to 'Wash 3'.

Wipe off any contaminating liquids using blue roll and IMS, ensuring that you can still read the label. Remove from the cabinet and place on the rocker for 20 mins (a timer should be used).

Remove from the cabinet and discard any materials that are no longer needed:

1×'Wash 2' flask (to which 20% distel should be added to make the total concentration of distel in the flask ≥2%).

When the third wash is complete, remove the flask from the rocker and return to the cabinet. Open the flask and transfer the AM from flask 'Wash 3' to the LHS tray.

Spongy layer (SL) removal—GB 2 441 939 patent (priority date 17-06-2006; granted 16-03-2011)—'Surgical Membranes Spread the AM out using the plastic forceps and use the sponge spears to detect the spongy layer (SL). The spears will stick to the spongy layer but not to the epithelial side. When the SL side has been determined place the AM SL side up and spread out.

Starting in the middle of the AM and using the blade holder, firmly but carefully penetrate through SL while taking care not to cut into the AM. Begin to peel back the SL from the AM, by carefully dragging, and not scraping, the SL material with the blade holder. Work along the line of cutting (left, right axis) peeling the SL as a continuous layer from the direction of the front of the hood to the back.

Using the plastic forceps transfer any loose SL to the 'Wash 3' flask.

There should be a brief wash and SL heck here to see if any remaining, unswelled SL material was left behind, and which can then be removed.

Once all SL has been removed place the AM in the flask labelled 'Post-filter raffinose'. Wipe off any contaminating liquids using blue roll and IMS, ensuring that you can still read the label. Transfer the flask to room 5061 (tissue culture) and place in an incubator for two hours (a timer should be used).

Remove from the cabinet and discard any materials that are no longer needed:

1×'Wash 3' flask (to which 20% distel should be added to make the total concentration of Distel in the flask ≥2%).

2× plastic forceps.
1× blade holder and no. 22 scalpel blade.
1×LHS tray
1× surgical scissors When manufacturing OmnigenTE, the thermolysin treatment methodology is inserted here prior to drying Amniotic membrane drying—GB priority (PCT) application 1309963.5 (priority date Apr. 6, 2013)—"Amniotic Membrane":

Materials and equipment required:
1× surgical scissors
1× Parafilm roll
1×50 mm trephine
1×30 mm trephine
1× metal forceps
2× plastic forceps
1× plastic tray
Pack of vacuum sealable wallets (cut each wallet in half)
Freeze drier
Vacuum sealer 20 minutes before the incubation ends the freeze drier should be prepared. Switch the machine on and remove the lid (place securely on the bench). Select 'Manual' and then 'freezing+warm-up VP' from the dropdown menu and press play.

Clean shelves using 2% Distel and 70% ethanol.

Once the incubation time has elapsed, remove the flask from the incubator and return to room 5059. Place flask on bench next to freeze drier.

Parafilm has 2 sides, one covered by a removable protective layer with the Parafilm logo on it. On the bench unroll a large section of the Parafilm and place protective layer side up. Cut the Parafilm so that the full AM can be spread over it, with space at the borders. Remove the protective layer.

Using plastic forceps remove the AM from the flask and place directly onto the Parafilm.

Spread the AM out epithelial side up and using the scissors cut the AM into as fewer pieces as possible; AM pieces should be kept as large as possible, whilst being able to fit within the constraints of the freeze drier.

Ensure that the AM pieces are fully spread out on parafilm and ensure any bubbles are smoothed out. Place these onto the freeze drier shelves and replace the lid.

Ensure all outlet valves are tightened and on the freeze drier select 'Manual' and then 'Main Drying'. Ensure a vacuum seal has been created. The AM should be dried in this way for 30 mins, a timer should be used.

After 30 mins, select 'Manual' and then 'Final Drying'. The AM should be dried in this way for 15 mins, a timer should be used.

After 15 mins, press stop and release the pressure valves. Once the pressure has been released remove the lid.

Remove the dried AM and place onto plastic tray. Place the 50 mm trephine as close to the edge of the AM as possible and press down hard. Turn in a single direction only and remove the trephine.

If the Parafilm is stuck to the AM use the metal forceps to gently tease them apart. Still using the forceps place the AM in a vacuum sealable wallet.

Ensuring as many 50 mm disks as possible have been cut. Use the 30 mm trephine to cut suitable remaining AM.

Once all AM are in wallets, open the vacuum sealer lid and turn on. Log the AM on the workspace database if you haven't already done so. Seal the wallets and label with date, 'P number' and sample number. Place together in cold room for future use.

TABLE 15

| | Disposables | | | |
|---|---|---|---|---|
| Quantity | Description | Supplier | Manufacturer | Catalogue Number |
| 7 | T175 non vented flask | Thermo Scientific Nunc | | 156502 |
| 1 | 1 L NaCl solution | Baxter | | UKF7124 |
| 1 | 500 ml sterile DPBS | Sigma Aldrich | | D8537 |

TABLE 15-continued

Disposables

| Quantity | Description | Supplier | Manufacturer | Catalogue Number |
|---|---|---|---|---|
| 1 | Metal forceps (sterile, individually wrapped) | | | |
| 1 | 10 ml syringe | Becton Dickinson | | 302188 |
| 1 | 50 ml syringe | Becton Dickinson | | |
| 1 | 19 G needle | Becton Dickinson | | 301750 |
| 2 | 0.2 µm filter | SLS | Millipore | |
| 1 | Square dish pack (sterile, individually wrapped) | Fisher Scientific | Thermo Scientific Nunc | 240835 |
| 5 | Plastic forceps (sterile, individually wrapped) | | | |
| 1 | Surgical scissors (sterile, individually wrapped) | | | |
| 1 | Size 22 blade (sterile, individually packaged) and custom holder | Fisher Scientific | Swann Morton | 0208 |
| 1 | No. 22 disposable scalpel | Fisher Scientific | Swann Morton | 0508 |
| 1 pack | Surgical sponge spears | | Eyetec Ophthalmic Products | 40-410 |
| 1 | 20 ml 'universal' tube | Sarstedt | | 60.9922.254 |
| 1 roll | Parafilm M large roll | SLS | Brand GMBH & Co | 7015 01 |
| 1 roll | Parafilm M small roll | Sigma Aldrich | Brand GMBH & Co | P7793 |
| 1 | 100 ml weighboat Spatula | Fisher Scientific | Fisher Scientific | FB61501 |
| 1 | 50 ml serological pipette | Greiner Bio-One Inc. | Greiner Bio-One Inc. | 768160 |
| 1 pack | Vacuum sealable wallets | | | |

TABLE 16

Additional Disposables

| Quantity | Description | Supplier | Catalogue Number |
|---|---|---|---|
| 1 | Marker pen | | |
| 1 | 6 L sharps bin | Sharpak Healthcare | SU02630 |
| Wash bottle | 70% IMS | MSS | HA-M0048 |
| Wash bottle | 2% Distel | MSS | LH-M0200E |
| 1 | Biohazard bag | MSS | |

TABLE 17

Equipment

| Quantity | Description | Supplier | Location |
|---|---|---|---|
| 1 | Timer | — | — |
| 1 | −80° C. freezer | | 5061 |
| 1 | Incubator (37° C., 5% CO2, 100% RH) | | 5061 |
| 1 | Fridge | | 5061 |
| 1 | 3D rocking platform STR 9 | | 5059 |
| 1 | Alpha 1-4 LSC Freeze dryer | Christ | 5059 |
| 1 | Envair Class II safety cabinet | Clugstons | 5059 |
| 1 | Pipette aid | | |
| 1 box | Xceed gloves (blue) | Starlabs | XC-INT-S/ XC-INT-M/ XC-INT-L |
| 1 box | Shieldskin gloves (orange) | Appleton Woods | KG976/ KG977/KG978 |
| | Decontamination tub Contaminated waste bin | | |
| 1 | Orved Multiple 315 Vacuum Sealer | Orved | 5059 |

TABLE 18

Reagents

| Quantity | Description | Supplier | Catalogue Number |
|---|---|---|---|
| 1 | 1 L Sterile sodium chloride solution (0.9%) | Baxter | UKF7124 |
| 1 | Sterile PBS | Sigma Aldrich | D8537 |
| 2 | 5 ml antibiotics/antifungal concentrate | Source Bioscience | 07-012 |
| 14.86 g | D-(+)-Raffinose pentahydrate | Acros Organics | 195670250 |

The invention claimed is:

1. A method of processing an amniotic membrane to provide a vacuum-dried amniotic membrane comprising the step of vacuum-drying the amniotic membrane, wherein the membrane is not frozen before or during the vacuum-drying step, and wherein when the membrane is reconstituted the membrane preparation releases epidermal growth factor (EGF) for a period of two or more days.

2. The method of claim 1 wherein the membrane is treated with one or more lyoprotectants before vacuum-drying.

3. The method according to claim 2 wherein the one or more lyoprotectant are selected from trehalose and raffinose.

4. The method of claim 1 wherein the lyoprotectant is trehalose or raffinose in combination with one or more further lyoprotectants.

5. The method of claim 1 wherein the amniotic membrane is treated with an antioxidant before vacuum-drying.

6. The method according to claim 5 wherein the antioxidant is epigallocatechin.

7. The method of claim 1 wherein the amniotic membrane is treated with further preservatives before the vacuum-drying step.

8. The method of claim 1 wherein the amniotic membrane is treated with thermolysin before vacuum-drying to provide a denuded amniotic membrane.

9. The method according to claim 8 further comprising the step of seeding cells onto the denuded amniotic membrane before vacuum-drying or after reconstituting the membrane.

10. A vacuum-dried amniotic membrane prepared using by the method according to claim 1.

11. A denuded vacuum-dried amniotic membrane prepared by the method according to claim 8.

12. A method of treating diseases or injuries of the eye comprising the step of applying a vacuum-dried amniotic membrane prepared by the method of claim 1 to the eye.

* * * * *